United States Patent [19]

Lasky et al.

[11] Patent Number: 5,484,891
[45] Date of Patent: Jan. 16, 1996

[54] SELECTIN LIGANDS

[75] Inventors: Laurence A. Lasky, Sausalito, Calif.; Yasuyuki Imai, Tokyo, Japan; Steven D. Rosen, San Francisco; Mark S. Singer, Berkeley, both of Calif.

[73] Assignees: Genentech, Inc., South San Francisco; The Regents of the University of California, Berkeley, both of Calif.

[21] Appl. No.: 18,994

[22] Filed: Feb. 18, 1993

Related U.S. Application Data

[60] Division of Ser. No. 834,902, Feb. 13, 1992, Pat. No. 5,304,640, which is a continuation-in-part of Ser. No. 695,805, May 6, 1991, Pat. No. 5,318,890.

[51] Int. Cl.$^6$ ............................ C07K 13/00; C07K 15/14
[52] U.S. Cl. ...................... 530/387.3; 530/350; 530/395; 435/7.2
[58] Field of Search ................. 530/350, 387.3, 530/395; 435/7.2

[56] References Cited

PUBLICATIONS

Bevilacqua et al., *Science* 243:1160 (1989).
Bevilacqua et al., *Proc. Natl. Acad. Sci. USA* 84, 9238 (1989).
Berg et al., *Immunol. Rev.* 108, 5 (1989).
Bonfanti et al., *Blood* 73, 1109 (1989).
Bowen et al., *J. Cell Biol.* 109, 421 (1989).
Butcher, *Am. J. Pathol.* 136, 3 (1990).
Butcher, E. C., *Curr. Top. Micro. Immunol.* 128, 85 (1986).
Camerini et al., *Nature* 342(6245), 78 (1989).
Corral et al., *Biochem. Biophys. Res. Commun.* 172, 1349 (1990).
Duijvestijn and Hamann, *Immunol. Today* 10, 23 (1989).
Gallatin et al., *Cell* 44, 673 (1986).
Geng et al., *Nature* 343:757 (1990).
Geoffroy and Rosen, *J. Cell. Biol.* 109, 2463 (1989).
Goelz et al. *Cell* 63(6), 1349 (1990).
Hattori et al., *J. Biol. Chem.* 264(14), 7768 (1989).
Hession et al., *Proc. Natl. Acad. Sci. USA* 87(5), 1673 (1990).
Johnston et al., *Cell* 56, 1033 (1989).
Larsen et al. *Cell* 63, 467 (1990).
Lasky et al., *Cell* 56, 1045 (1989).
Lowe et al. *Cell* 63, 475 (1990).
McEver et al., *J. Biol. Chem.* 259, 9799 (1984).
Moore et al., *J. Cell Biol.* 112, 491 (1991).
Phillips et al., *Science* 250(4984), 1130 (1990).
Polley et al., *Proc. Natl. Acad. Sci. USA* 88, 6224 (1991).
Rosen et al., *Science* (Wash., D.C.) 228, 1005 (1985).
Rosen et al., *J. Immunol.* 142, 1895 (1989).
Siegelman et al., *Science* (Wash., D.C.) 243, 1165 (1989).
Siegelman et al., *Proc. Natl. Acad. Sci. USA* 86, 5562 (1989).
Stoolman, *Cell* 56, 907 (1989).
Stoolman et al., *J. Cell Biol.* 99, 1535 (1984).
Stoolman et al., *Blood* 70, 1842 (1987).
Tiemeyer et al. *Proc. Natl. Acad. Sci. USA* 88(4), 1138–42 (1991).
True et al., *J. Cell Biol.* 11, 2757–2764 (1990).
Walz et al. *Science* 250(4984), 1132 (1990).
Watson et al., *J. Cell Biol.* 110, 2221 (1990).
Watson et al., *Nature* 349, 164–167 (1991).
Woodruff et al., *Annu. Rev. Immunol.* 5, 201 (1987).
Yednock and Rosen, *Adv. Immunol.* 44, 313 (1989).
Gallatin et al., *Nature* 304, 30–34 (1983).
Stoolman and Rosen, *J. Cell. Biol.* 96, 722–729 (1983).
Tedder et al., *J. Exp. Med.* 170(1), 123–133 (1989).
Teder et al., *J. Immunol.* 144, 532–540 (1989).

*Primary Examiner*—Richard A. Schwartz
*Assistant Examiner*—David Guzo
*Attorney, Agent, or Firm*—Ginger R. Dreger

[57] ABSTRACT

The invention relates to glycoprotein ligands of selectins. The invention further relates to methods and means for preparing and to nucleic acids encoding these ligands. The invention further concerns a method of treating a symptom or condition associated with excessive binding of circulating leukocytes to endothelial cells by administering to a patient in need of such treatment a glycoprotein ligand of a selectin.

9 Claims, 12 Drawing Sheets

```
  1 CTGACCTTGT TCCAGTGCCA CCATGAAATT CTTCACTGTC CTGCTATTTG TCAGTCTTGC
    GACTGGAACA AGGTCACGGT GGTACTTTAA GAAGTGACAG GACGATAAAC AGTCAGAACG
  1                     METLYSPH EPHETHRVAL LEULEUPHEV ALSERLEUALA

61 TGCCACCTCT CTTGCTCTCC TGCCTGGGTC AAAGATGAA CTTCAAATGA AGACTCAGCC
    ACGGTGGAGA GAACGAGAGG ACGGACCCAG GTTTCTACTT GAAGTTTACT TCTGAGTCGG
 14 ALATHRSER LEUALALEUL EUPROGLYSE RLYSASPGLU LEUGLNMETL YSTHRGLNPRO
                N-terminus 121 CACAGATGCC ATTCCAGCTG CCCAGTCCAC TCCCACCAGC TACACCAGTG AGGAGAGTAC
    GTGTCTACGG TAAGGTCGAC GGGTCAGGTG AGGGTGGTCG ATGTGGTCAC TCCTCTCATG
 34 THRASPALA ILEPROALAA LAGLNSERTH RPROTHRSER TYRTHRSERG LUGLUSERTHR 181 TTCCAGTAAG GACCTTTCCA AGGAGCCTTC CATCTTCAGA GAAGAGCTGA TTTCCAAAGA
    AAGGTCATTC CTGGAAAGGT TCCTCGGAAG GTAGAAGTCT CTTCTCGACT AAAGGTTTCT
 54 SERSERLYS ASPLEUSERL YSGLUPROSE RILEPHEARG GLUGLULEUI LESERLYSASP 241 TAATGTGGTG ATAGAATCTA CCAAGCCAGA GAATCAAGAG GCCCAGGATG GGCTCAGGAG
    ATTACACCAC TATCTTAGAT GGTTCGGTCT CTTAGTTCTC CGGGTCCTAC CCGAGTCCTC
 74 ASNVALVAL ILEGLUSERT HRLYSPROGL UASNGLNGLU ALAGLNASPG LYLEUARGSER
```

```
  1 CTGACCTTGT TCCAGTGTCC CCATGAATT  CTTCACTGTC CTGCTATTTG TCAGTCTTGC
    GACTGGAACA AGGTCACGGT GGTACTTAA  GAAGTGACAG GACGATAAAC AGTCAGAACG
  1                       METLYSPH   EPHETHRVAL LEULEUPHEV A LSER LEUALA

61 TGCCACCTCT CTGCTCTCC  TGCCTGGGTC CAAAGATGAA  CTTCAAATGA AGACTCAGCC
    ACGGTGGAGA GAACGAGAGG ACGGACCCAG GTTTCTACTT  GAAGTTTACT TCTGAGTCGG
 14 ALA THR SER LEUALALEUL EUPROGLY   LYSASPGLU  LEUGLNMETL YS THR GLN PRO
                         N-terminus 121 CACAGATGCC ATTCCAGCTG CCCAGTCCAC TCCCACCAGC  TACACCAGTG AGGAGAGTAC
    GTGTCTACGG TAAGGTCGAC GGGTCAGGTG AGGGTGGTCG  ATGTGGTCAC TCCTCTCATG
 34 THR ASPALA ILEPROALAA LA GLN SER TH R PRO THR SER  TYR THR SER G LU GLU SER THR 181 TTCCAGTAAG GACCTTTCCA AGGAGCCTTC CATCCTTCAGA GAAGAGCTGA TTTCCAAAGA
    AAGGTCATTC CTGGAAAGGT TCCTCGGAAG GTAGAAGTCT CTTCTCGACT AAAGGTTTCT
 54 SER SER LYS ASPLEU SER  YSGLUPRO SE R ILEPHEARG GLUGLULEUI L SER LYSASP 241 TAATGTGGTG ATAGAATCTA CCAAGCCAGA GAATCAAGAG GCCCAGGATG GGCTCAGGAG
    ATTACACCAC TATCTTAGAT GGTTCGGTCT CTTAGTTCTC CGGGTCCTAC CCGAGTCCTC
 74 ASNVALVAL  ILEGLU SER T HR LYSPROGL UASNGLNGLU ALAGLNASPG LYLEUARG SER
```

FIG. 4A

```
301  CGGGTCATCT  CAGCTGGAAG  AGACCACAAG  ACCCACCACC  TCAGCTGCAA  CCACCCTCAGA
     GCCCAGTAGA  GTCGACCTTC  TCTGGTGTTC  TGGGTGGTGG  AGTCGACGTT  GGTGGAGTCT
 94     GLY SER  SER      GLN LEU GLU GLU GLU  LEU THR HIS THR ARG  ALA LEU ALA LEU ALA  THR HIS THR HIS ARG SER GLU

361  GGAAAATCTG  ACCAAGTCAA  GCCAGACAGT  GGAGGAAGAA  CTGGGTAAAA  TAATTGAAGG
     CCTTTTAGAC  TGGTTCAGTT  CGGTCTGTCA  CCTCCTTCTT  GACCCATTTT  ATTAACTTCC
114     GLU ASN LEU  THR LYS SER  SER GLU ARG  GLN THR ARG VAL  LEU GLY LEU GLU  LEU ILE GLU GLY

421  ATTTGTAACT  GGTGCAGAAG  ACATAATCTC  TGGTGCCAGT  CGTATCACGA  AGTCATGAAG
     TAACATTGA   CCACGTCTTC  TGTATTAGAG  ACCACGGTCA  GCATAGTGCT  TCAGTACTTC
134     PHE VAL THR  GLY ALA GLU  ASP ILE ILE SER  GLY ALA SER  ARG ILE THR  LYS SER

481  ACAAAAACAC  CTAACCACTA  AGTCCCATGC  TAGGTGGTGC  CTTCATCAGC  CACATTCTGC
     TGTTTTTGTG  GATTGGTGAT  TCAGGGTACG  ATCCACCACG  GAAGTAGTCG  GTGTAAGACG

541  TCATCTGACC  ACCACCTCTC  AGTCTGCCCT  TTGATGTCTT  ACATTAAAGT  ATTGCAACCT
     AGTAGACTGG  TGGTGGAGAG  TCAGACGGGA  AACTACAGAA  TGTAATTTCA  TAACGTTGGA

601  AAAAAAAA
     TTTTTTTT
```

FIG. 4B 0.7kb —

SELECTIN LIGANDS

This is a divisional of application Ser. No. 07/834,902 filed on 13 Feb. 1992, now U.S. Pat. No. 5,304,640 which is a continuation-in-part of U.S. application Ser. No. 07/695, 805 filed 6 May 1991. now U.S. Pat. No. 5,318,830.

BACKGROUND OF THE INVENTION

I. Field of the Invention

The present invention relates to endothelial selectin ligands. The invention further relates to methods and means for preparing and to nucleic acids encoding these ligands.

II. Description of Background and Related Art

Lymphocytes are mediators of normal tissue inflammation as well as pathologic tissue damage such as occurs in rheumatoid arthritis and other autoimmune diseases. In order to fully exploit the antigenic repertoire of the immune system, vertebrates have evolved a mechanism for distributing lymphocytes with diverse antigenic specificities to spatially distinct regions of the organism [Butcher, E. C., Curr. Top. Micro. Immunol. 128, 85 (1986); Gallatin et al., Cell 44, 673 (1986); Woodruff et al., Immunol. Today 10, 23 (1989); Yednock et al., Adv. Immunol. 44, 313 (1989)].

This mechanism involves the continuous recirculation of the lymphocytes between the blood, where the cells have the greatest degree of mobility, and the lymphoid organs, where the lymphocytes encounter sequestered and processed antigen.

It has been recognized for some time that the trafficking of lymphocytes from the blood into secondary lymphoid organs, such as lymph nodes (LN) and gut-associated Peyer's patches (PP), is initiated by an adhesive interaction with the specialized endothelial cells of high endothelial venules (HEY) [Berg et al., Immunol. Rev. 108, 5 (1989); Duijvestijn and Hamann, Immunol. Today 10, 23 (1989); Woodruff et al., Annu, Rev. Immunol. 5, 201 (1987); Yednock and Rosen, Adv. Immunol. 44, 313 (1989); Stoolman, Cell 56, 907 (1989)]. Considerable evidence indicates that the lymphoid organ-selective migration or "homing" of lymphocytes is dictated in large part by organ-specific binding of lymphocytes to HEY [Butcher (1986), Supra]. Operationally, the lymphocyte-associated molecules underlying the organ-selective interaction with HEV are termed "homing receptors" while the cognate endothelial molecules are known as "HEV ligands" [Gallatin et al. (1986), Supra; Rosen, Curr. Opin. Cell. Biol. 1, 913 (1989)]. The endothelial HEV ligands are postulated to be distinctive for the different lymphoid organs and as such are proposed to be responsible for regulating the lymphocyte populations to enter each class of lymphoid organ [Butcher, Am. J. Pathol. 136, 3 (1990)]. A characterization of the detailed molecular mechanisms underlying lymphocyte trafficking is interesting from both a scientific and a clinical standpoint, since similar adhesive processes may be involved in both the normal and pathogenic forms of leukocyte inflammation [Watson et al., Nature 349, 164–167 (1991)].

Of the homing receptors, the most thoroughly studied is a receptor initially termed peripheral lymph node homing receptor (pnHR). This receptor was first defined in the murine system by the MEL-14 monoclonal antibody (mAb), an antibody that was found to recognize an about 90 kD leukocyte surface antigen (referred to as gp90$^{MEL}$) [Gallatin et al., Nature 303, 30 (1983)]. This antibody was found to block the lymphocyte adhesion to HEV of peripheral and mesenteric lymph nodes in the Stamper-Woodruff in vitro adherence assay and to prevent in vivo migration to lymph nodes. A homing function for gp90$^{MEL}$ was definitely shown by the finding that detergent solubilized and soluble recombinant forms of the receptor can selectively block adhesive sites for lymphocytes on LN but not those on PP HEY [Geoffroy and Rosen, J. Cell. Biol. 109, 2463 (1989)].

Molecular cloning of cDNAs encoding the murine and human gp90$^{MEL}$ receptors revealed a transmembrane protein with a calcium-type (C-type) lectin domain at its extracellular amino terminus, followed by an EGF motif, two complement regulatory motifs related to those found in proteins with complement-binding activity, a transmembrane domain, and a short cytosolic tail [Lasky et al., Cell 56, 1045 (1989); Siegelman et al., Science (Wash., D.C.) 243, 1165 (1989); Siegelman et al., Proc. Natl. Acad. Sci. USA 86, 5562 (1989); Tedder et al., J. Exp. Med. 170(1) 123 (1989); Tedder et al., J. Immunol. 144, 532 (1989); Bowen et al., J. Cell Biol. 109, 421 (1989); Camerini et al., Nature 342(6245), 78 (1989); copending application Ser. No. 315, 015 filed 23 Feb. 1989; WO 91/08298 published 13 Jun. 1991].

Other researchers identified another molecule associated with neutrophil adhesion. It was proposed that this molecule, termed the endothelial leukocyte adhesion molecule ELAM-1, is an inducible adhesion molecule whose role may be to mediate the attachment of neutrophils to venular endothelial cells adjacent to sites of inflammation [Bevilacqua et al., Proc. Natl. Acad. Sci. USA 84, 9238 (1989); Hession et al., Proc. Natl. Acad. Sci. USA 87 (5), 1673 (1990)].

Investigations of the proteins contained in the alpha granules of platelets led to the discovery of a further adhesion molecule variously termed granular membrane protein-140 (GMP- 140), platelet activation dependent granule external membrane protein (PADGEM) or CD62 [McEver et al., J. Biol. Chem. 259, 9799 (1984); Bonfanti et al., Blood 73, 1109 (1989); Hattori et al., J. Biol. Chem. 264(14), 7768 (1989)]. The cDNA sequence encoding this receptor was determined by Johnston et al., Cell 56, 1033 (1989).

Comparison of their amino acid sequences revealed that these three adhesion molecules are related in a highly striking and compelling manner. Their common mosaic structure consists of a calcium dependent lectin or carbohydrate-binding motif, an epidermal growth factor-like (EGF) motif, and variable numbers of a complement regulator (CR) motif. The ordered conjunction of these motifs has given rise to the name LEC-CAM (Lectin Egf Complement regulatory-Cell Adhesion Molecule) for this new family of leukocyte endothelial cell adhesion molecules [Stoolman, Cell 56:907 (1989)]. Alternatively, the name "selectin" has been applied to this family [Bevilacqua et al., Science 243:1160 (1989); Geng et al., Nature 343:757 (1990)].

The three members of the LEC-CAM or selectin family of cell adhesion molecules are: L-selectin (a.k.a. peripheral lymph node homing receptor (pnHR), LEC-CAM-1, LAM-1, gp90$^{MEL}$, gp100$^{MEL}$, gp110$^{MEL}$, MEL-14 antigen, Leu-8 antigen, TQ-1 antigen, DREG antigen), E-selectin (LEC-CAM-2, LECAM-2, ELAM-1) and P-selectin (LEC-CAM-3, LECAM-3, GMP-140, PADGEM). These receptors will further on be referred to as "selectins". The structures of the selectin family members and of the genes encoding them are illustrated in FIGS. 1 and 2, respectively.

The finding that simple monomeric sugars, such as mannose-6-phosphate (M6P) and fructose-1-phosphate, can block the interactions of murine and human lymphocytes with HEY of peripheral lymph nodes (pln) [Stoolman et al., J. Cell Biol. 96, 722 (1983); Stoolman et al., J. Cell Biol. 99, 1535 (1984); Stoolman et al., Blood 70, 1842 (1987)] suggested that the endothelial ligand recognized by L-selectin is carbohydrate-based. In one series of experiments, Rosen and colleagues demonstrated that the homing receptor-dependent binding of lymphocytes to pln HEV was abolished by either in vitro or in vivo treatment with broad spectrum sialidases [Rosen et al., Science (Wash., D.C.) 228, 1005 (1985); Rosen et al., J. Immunol. 142, 1895 (1989)]. Because this enzyme selectively removes terminal sialic acid residues from oligosaccharides, these results strongly implied that sialic acid was a critical element for recognition.

The nature of the endothelial molecule(s) recognized by L-selectin was subsequently probed with a unique recombinant chimera, consisting of the extracellular domain of L-selectin joined to the hinge, CH2 and CH3 regions of the human IgG1 heavy chain [see WO 91/08298 published 13 Jun. 1991 for the chimera, and Watson et al., J. Cell Biol. 110, 2221 (1990) for its use as a probe for adhesive ligands of lymph node high endothelial venules]. Initial studies with this so-called receptor-immunoglobulin chimera demonstrated that it could adhere to (a) peripheral and mesenteric lymph node-specific HEV ligand(s) in cell blocking and immunohistochemical experiments [Watson et al. (1990), Supra]. The immunohistochemical recognition of this HEV ligand was abolished by treatment of lymph node sections with sialidase, suggesting that a component of the carbohydrate recognized by L-selectin was sialic acid-like and further accentuated the importance of the lectin domain in L-selectin-mediated adhesion [Rosen et al., Science (Wash. D.C.) 228, 1005–1007 (1985); Rosen et al. (1989), Supra, and True et al., J. Cell Biol. 11, 2757–2764 (1990)]. These results demonstrated the specificity of the L-selectin-immunoglobulin chimera for the pln HEV ligand and established that the ligand expresses carbohydrate residues that are essential for homing receptor-mediated cell adhesion.

A recent series of publications confirmed that the E-selectin ligand also has a carbohydrate character. Several laboratories, adopting a wide range of approaches, have concluded that an E-selectin ligand is a carbohydrate known as sialyl Lewis$^x$ (sLex) or a closely related structure known as CD65 or VIM-2 [NeuAca2-3Galb1-4(Fuca1-3)GlcNAcb1]. Lowe et al.[Cell 63, 475 (1990)], transfected non-myeloid cells with an a1,¾ fucosyltransferase and generated ligand activity for E-selectin, which was correlated with the expression of the Slex determinant. Goeltz et al. [Cell 63(6), 1349 (1990)] identified and cloned an a1,3 fucosyltransferase that appeared to be involved in the synthesis of the actual ELAM-1 ligand in myeloid cells. Using more direct approaches, Phillips et al. [Science 250(4984), 1130 (1990)] and Walz et al. [Science 250(4984), 1132 (1990)] were able to show inhibition of E-selectin dependent adhesion with either Slex-containing glycoconjugates or antibodies to Slex. The critical participation of both the sialic acid and fucose moieties in ligand activity were demonstrated in these studies. Finally, Tiemeyer et al. [Proc. Natl. Acad. Sci. USA (1991)] purified several myeloid-derived glycolipids that had ligand activity for E-selectin transfected cells in a solid-phase assay. Mass spectroscopic analysis of purified, E-selectin binding glycolipid revealed that the minimal structure necessary for activity was a silylated lactosamine with a second internal N-acetyllactosamine unit containing an a1,3-linked fucose on the N-acetylglucosamine (CD65). As was true for the Slex determinant, both the sialic acid and fucose were essential for binding activity of the putative ligand.

Progress has also been made in the identification of ligands for P-selectin. Larsen et al. [Cell 63, 467 (1990)] have implicated the Lex determinant [Galb1–4(a1–3Fuc)GlcNAc] as an important element of the P-selectin ligand on myeloid cells. However, sialic acid is also required for full ligand activity, probably in an a2,3 linkage [Corral et al., Biochem. Biophys. Res. Commun. 172, 1349 (1990); Moore et al., J. Cell Biol. 112, 491 (1991)]. There is a possibility that the ligand for P-selectin is the same or very similar to that for E-selectin, especially since both selectins bind to a very similar spectrum of cells types [Polley et al., Proc. Natl. Acad. Sci. USA 88, 6224 (1991)].

The remarkable homology in selectin structures as well as the already demonstrated similarities in the ligands suggest that the ligands will have related and yet subtlely different structures.

An object of the present invention is to provide a method for the purification of a selectin ligand.

Another object of the invention is to provide purified selectin, specifically L-selectin ligands.

A further object of the present invention is to provide nucleic acid sequences encoding selectin glycoprotein ligands.

It is another object to determine the amino acid sequences of the selectin ligands, and to identify the (O- and N-linked) glycosylation sites on these ligands.

A still further object is to enable the preparation of amino acid sequence and/or glycosylation variants of selectin ligands, not otherwise found in nature.

In a still further aspect, the invention provides a method of designing selectin inhibitors, mimicking carbohydrate based determinants of the selectin ligands.

These and further objects of the present invention will be apparent for one skilled in the art.

SUMMARY OF THE INVENTION

Our initial analysis of the HEV-associated ligand took advantage of a unique aspect of HEV metabolism. Early work by Andrews et al. [J. Cell Sci. 57, 277 (1982)] had shown that HEV in situ were distinctive in that they incorporated high amounts of inorganic sulfate into macromolecules. We have, therefore, analyzed the ability of L-selectin-IgG chimera to precipitate inorganic sulfate-labeled material from lymph nodes labeled with $^{35}$S-sulfate in organ culture. A prominent 50 kD component and a weaker 90 kD molecule ($Sgp^{50}$ and $Sgp^{90}$) were precipitated from lymph nodes but were not present in any other organ tested. The precipitation of these components with the L-selectin-IgG chimera was shown to be calcium-dependent, sensitive to both the MEL-14 mAb and specific carbohydrates. This reaction could be abolished by treatment of the sulfate-labeled proteins with sialidase or by inclusion of the carbohydrate polymer fucoidin in the reaction. Finally, a monoclonal antibody, termed MECA-79, which selectively reacts with so-called "vascular addressins" of pln HEV and blocks adhesivity for lymphocytes [Streeter et al., J. Cell. Biol. 107, 1853 (1988)], precipitated both components. A preliminary biochemical analysis revealed that the ~50 kD and ~90 kD L-selectin ligands were trypsin-sensitive glycoproteins, containing predominantly O-linked chains. [See co-pending patent application Ser. No. 07/695,805 filed 6 May 1991, the parent of the present application, and Imai et. al., J. Cell Biol. 113, 1213 (1991).] The finding of O-linked chains is of interest in view of the evidence that O-linked regions cause cell surface glycoproteins to be highly extended and rigid structures [Jentoft et al., Trends in Biochem Sci. 15, 291 (1990)]) and thus ideally positioned to perform recognition functions. Fucose, sulfate and sialic acid were found in the O-linked chains of these molecules, and it is believed that fucose, like sialic acid, is required for full ligand activity.

In order to further characterize the nature of the endothelial ligand recognized by L-selectin, we have taken the novel approach of affinity purifying the sulfated ~50 kD HEV glycoprotein with the L-selectin-IgG chimera. The purified glycoprotein has been subjected to N-terminal amino acid sequencing, and this sequence information has been utilized to clone a cDNA encoding the protein component of this L-selectin ligand. It has been found that the cDNA encodes a novel, highly O-linked (mucin-like) glycoprotein that appears to function as a scaffold that presents carbohydrates to the lectin domain of L-selectin. Details of the experimental work along with the findings and their interpretation are provided in the examples.

The present invention concerns an isolated nucleic acid molecule comprising a nucleotide sequence encoding a selectin ligand.

Such nucleic acid molecule preferably comprises a nucleotide sequence able to hybridize to the complement of a nucleotide sequence encoding a protein having the amino acid sequence shown in FIG. 4 (SEQ. ID. No.:2).

In another embodiment, the nucleic acid molecule comprises a nucleotide sequence encoding a selectin ligand protein having an amino acid sequence greater than about 40% homologous with the amino acid sequence shown in FIG. 4 (SEQ ID. No.:2).

In a further embodiment, the nucleic acid molecule is selected from the group consisting of:

(a) a cDNA clone having a nucleotide sequence derived from the coding region of a native selectin ligand gene;

(b) a DNA sequence able to hybridize under low stringency conditions to a clone of (a); and (c) a genetic variant of any of the DNA sequences of (a) and (b) which encodes a glycoprotein possessing a biological property of a naturally occurring ligand of a selectin molecule.

The nucleic acid molecule of the invention may further comprise a nucleotide sequence encoding an immunoglobulin constant domain.

In another aspect, the present invention concerns an expression vehicle comprising a nucleotide sequence encoding a selectin ligand, preferably an L-selectin ligand, operably linked to control sequences recognized by a host cell transformed with the vehicle.

In a further aspect, the invention relates to a host cell transformed with the above-described expression vehicle, and methods for culturing such transformed host cells to express a selectin ligand.

In a still further aspect, the present invention concerns an isolated polypeptide comprising an amino acid sequence possessing a biological property of a naturally occurring ligand of a selectin molecule. Such polypeptide may comprise the extracellular region of an endothelial cell surface glycoprotein. In another embodiment, the polypeptide is Sgp50 or Sgp90.

The polypeptide of the present invention preferably comprises an amino acid sequence having a sterical structure allowing for the presentation of a selectin-binding moiety to its receptor.

In a specific embodiment, the foregoing polypeptide comprises an amino acid sequence encoded by a nucleic acid able to hybridize to the complement of a nucleotide sequence encoding the protein having the amino acid sequence shown in FIG. 4 (SEQ ID. No.2).

In a further specific embodiment, the above-described polypeptide is a native selectin ligand substantially free of other proteins of the same animal species in which it naturally occurs.

In a still further aspect, the invention concerns a polypeptide as hereinbefore defined, further comprising an immunoglobulin constant domain sequence.

In a different aspect, the invention concerns a composition comprising an amount of a polypeptide (glycoprotein selectin ligand) as hereinabove defined, effective in blocking the binding of a corresponding selectin receptor to its native ligand, in admixture with a non-toxic, pharmaceutically acceptable excipient.

In another aspect, the invention relates to a method of treating a symptom or condition associated with excessive binding of circulating leukocytes to endothelial cells comprising administering to a patient in need of such treatment a polypeptide as hereinabove defined in an amount effective in blocking the binding of an L-selectin receptor on a circulating leukocyte to its endothelial ligand.

In still another aspect, the invention concerns an antibody immunoreactive with the protein part of a selectin ligand. Preferred antibodies bind the respective selectin ligand but will not substantially cross-react with any other known ligands, and will prevent the selectin ligands from binding to their receptors. The anti-selectin ligand antibodies may be immobilized, and in this form are, for example, useful for the detection or purification of the selectin ligands of the present invention.

In a further aspect, the invention relates to a method for determining the presence of a selectin ligand, comprising a) hybridizing a nucleic acid encoding a selectin ligand or a complement of such nucleic acid to a test sample of nucleic acid; or b) performing the polymerase chain reaction with primers based on a nucleic acid encoding a selectin ligand; and c) determining the presence of a selectin ligand.

In a still further aspect, the invention provides a method for the purification of a selectin ligand comprising absorbing the ligand to a chimera comprising the corresponding selectin and an immunoglobulin heavy chain sequence.

The invention further concerns a method for presenting a selectin-binding moiety to a corresponding selectin by binding such moiety to the protein core of a selectin ligand glycoprotein.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 4 (Parts A and B) shows the nucleotide and the encoded amino acid sequence of the core protein of an endothelial ligand for L-selectin. (SEQ. ID. No.: 2) The unshaded box illustrates a Kozak translational initiation site surrounding the first methionine codon. The dotted underlined amino acid sequence beginning at residue 20 corresponds with the amino acid sequence determined by N-terminal sequencing of the L-selectin purified ligand (FIG. 3B) with the exception of a THR at position 34 (a MET in the N-terminal sequence). The serine and threonine residues in the predicted amino acid sequence are shown in shaded boxes.

DETAILED DESCRIPTION OF THE INVENTION

I. DEFINITIONS

Figure 1:
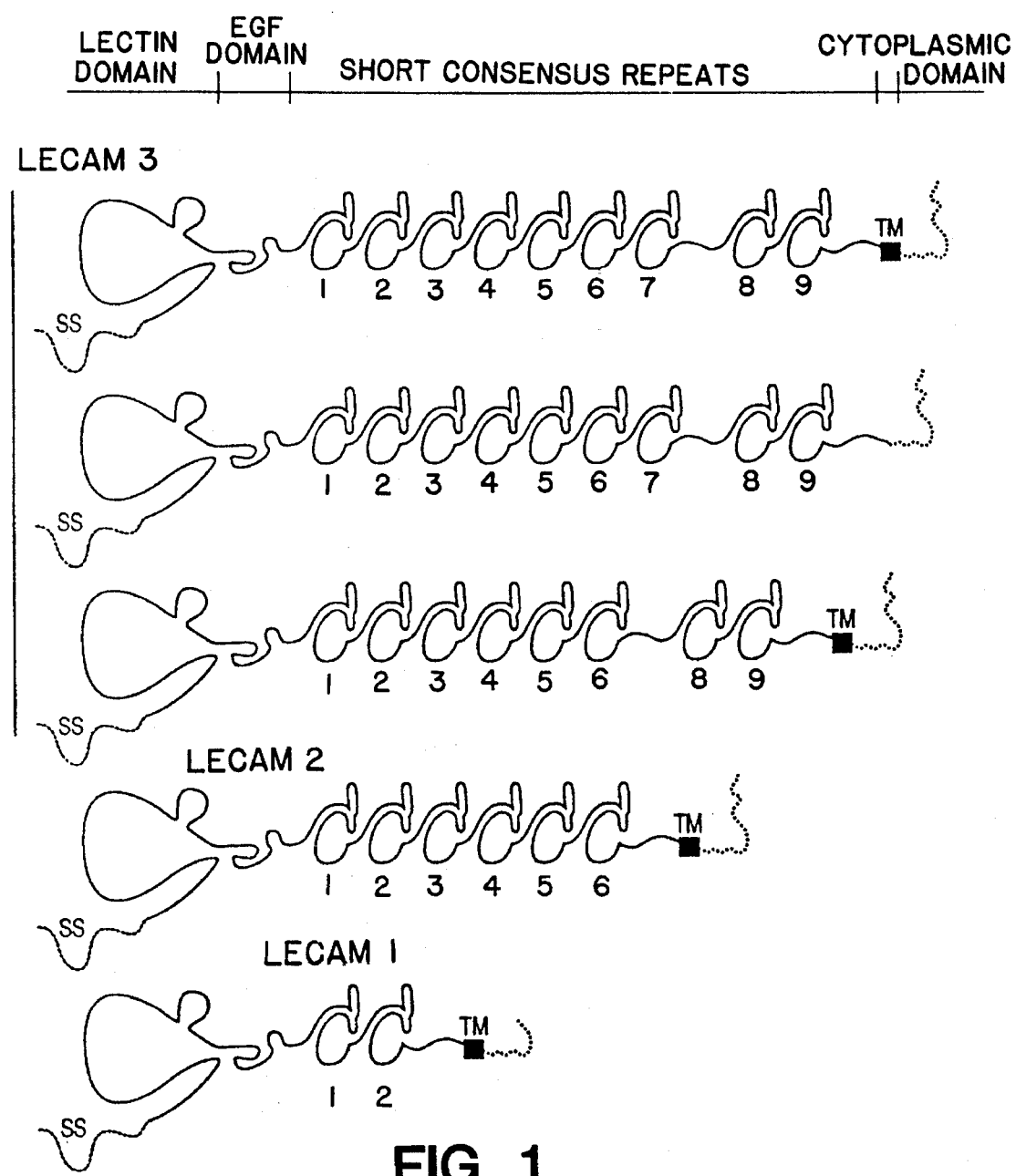
FIG. 1 illustrates the structures of the selectin (LEC-CAM) family members as determined by cDNA cloning. Illustrated are the structures for L-selectin, E-selectin and P-selectin. The lectin, epidermal growth factor (EGF), and multiple short consensus repeats (SCRs) are shown with hypothetical disulfide bond structures as first proposed for GMP-140 by Johnston et al., Cell 56, 1033 (1989). An N-terminal sequence is also shown (subsequently cleaved in the mature protein) as well as a hydrophobic transmembrane spanning anchor (TM) and cytoplasmic tail. Two other forms of P-selectin are also illustrated, one with a deleted scr-7 domain and another with a deleted membrane spanning anchor.
Figure 2:
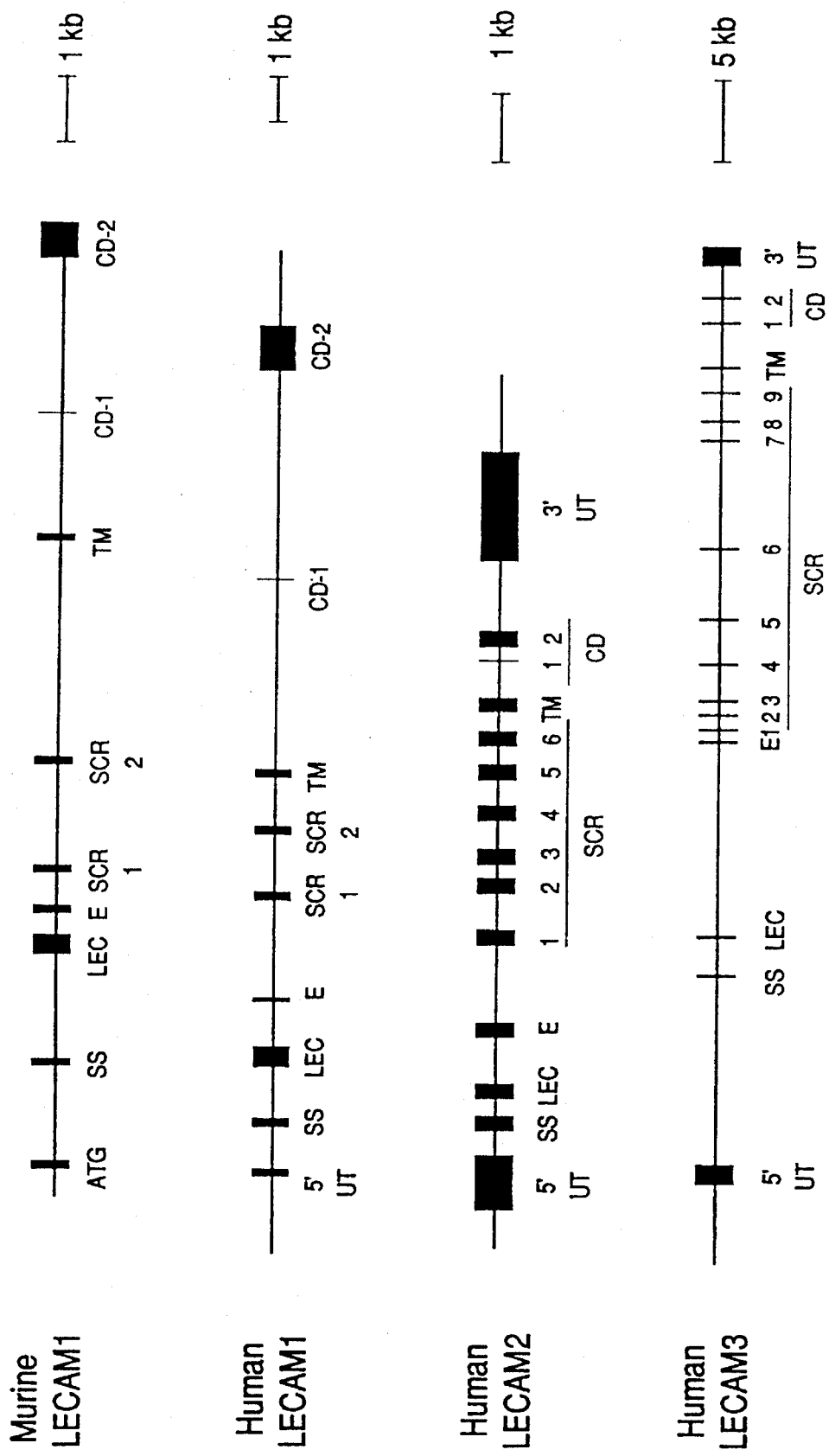
FIG. 2 shows the structure of the genes encoding members of the selectin family. Illustrated are the genomic structures encoding both human and murine L-selectin, human E-selectin and human P-selectin. The dark boxes show exons that encode the various structural motifs, including the start codon for the murine gene (ATG), the signal sequence (SS), the lectin (LEC), epidermal growth factor (E), short concensus repeats (SCR), transmembrane anchor (TM) and cytoplasmic domains (CD) and the intervening regions encode the introns that separate these protein coding domains. In the human, all three selectin genes are within 200 kilobases of each other on the long arm of chromosome 1 near a locus encoding a family of proteins that all contain variable numbers of the short SCR exon. The murine L-selectin is also encoded on murine chromosome 1 in a region syntonic to that found in the human chromosome 1 homologue.

The term "selectin ligand" and its grammatical variants, are used to refer to a polypeptide having a qualitative biological property in common with a naturally occurring ligand of a selectin molecule.

"Biological property" in this context means an in vivo effector or antigenic function or activity that is directly or indirectly performed by a naturally occurring ligand of a selectin molecule, or by any subsequence thereof. Effector functions include receptor binding, any enzyme activity or enzyme modulatory activity, any carrier binding activity, any hormonal activity, any activity in promoting or inhibiting adhesion of cells to extracellular matrix or cell surface molecules, or any structural role. The antigenic functions essentially mean the possession of an epitope or antigenic site that is capable of cross-reacting with antibodies raised against a naturally occurring ligand of a selectin molecule.

"Biologically active" selectin ligands share an effector function of a naturally occurring ligand of a selectin molecule, which may, but need not, in addition possess an antigenic function.

The selectin ligand as defined for the purpose of the present invention, preferably comprises a sequence having the qualitative ability to bind a selectin, and having a highly O-linked mucin-type, rod-like structure allowing for the presentation of its carbohydrates to the lectin domain of a selectin.

In a further preferred embodiment, the selectin ligand comprises an amino acid sequence encoded by a nucleotide sequence able to hybridize (under low stringency conditions) to the complement of a nucleotide sequence encoding the protein having the amino acid sequence shown in FIG. 4 (SEQ. ID. No.:2).

The amino acid sequence of the protein core of the selectin ligand is preferably greater than about 40% homologous, more preferably greater than about 60% homologous, still more preferably greater than about 70% homologous, even more preferably greater than about 80%, and most preferably at least about 90% homologous with the amino acid sequence shown in FIG. 4 (SEQ. ID. No.:2).

"Homologous" is defined as the percentage of residues in the candidate amino acid sequence that are identical with the residues in the amino acid sequence shown in FIG. 4 (SEQ. ID. No.:2) after aligning the sequences and introducing gaps, if necessary, to achieve the maximum percent homology.

The term "selectin ligand" specifically encompasses amino acid and glycosylation variants of native selectin ligands, as well as their derivatives, such as those obtained by covalent modifications, provided that they qualitatively retain a biological property possessed by a naturally occurring ligand of a selectin molecule, and preferably the qualitative ability to bind their receptors.

The term specifically encompasses glycoproteins comprising an amino acid sequence having a biological property in common with a naturally occurring ligand of a selectin fused to a stable plasma protein.

"Stable plasma proteins" are proteins typically having about 30 to about 2000 residues, which exhibit in their native environment an extended half-life in the circulation, i.e. a half-life greater than about 20 hours. Examples of suitable stable plasma proteins are immunoglobulins, albumin, lipoproteins, apolipoproteins and transferrin. The amino acid sequence having a qualitative biological property in common with a naturally occurring selectin ligand is generally fused C-terminally to a stable plasma protein sequence, e.g. immunoglobulin constant domain sequence.

The term "immunoglobulin" generally refers to polypeptides comprising a light or heavy chain usually both disulfide bonded in the native "Y" configuration, although other linkage between them, including tetramers or aggregates thereof, is within the scope hereof.

Immunoglobulins (Ig) and certain variants thereof are known and many have been prepared in recombinant cell culture. For example, see U.S. Pat. No. 4,745,055; EP 256,654; Faulkner et al., Nature 298:286 (1982); EP 120, 694; EP 125,023; Morrison, J. Immun. 123:793 (1979); Köhler et al., Proc. Nat'l. Acad. Sci. USA 77:2197 (1980); Raso et al., Cancer Res, 41:2073 (1981); Morrison et al., Ann. Rev. Immunol. 2:239 (1984); Morrison, Science 229:1202 (1985); Morrison et al., Proc. Natal. Acad. Sci. USA 81:6851 (1984); EP 255,694; EP 266,663; and WO 88/03559. Reassorted immunoglobulin chains also are known. See for example U.S. Pat. No. 4,444,878; WO 88/03565; and EP 68,763 and references cited therein. Ligand binding protein-stable plasma protein chimeras, and specifically L-selectin-immunoglobulin chimeras are, for example, disclosed in WO 91/08298 published 13 Jun. 1991. The immunoglobulin moiety in the chimera of the present invention may be obtained from $IgG_1$, $IgG_2$, $IgG_3$, or $IgG_4$ subtypes, IgA, IgE, IgD or IgM, but preferably $IgG_1$ or $IgG_3$.

Selectin, such as L-selectin binding can, for example, be assayed by determining the binding of radiolabeled (e.g. $^{35}$S-labeled) ligands to immobilized receptor-immunoglobulin chimera, in the presence or absence of soluble inhibitors, essentially as described by Imai et al., J. Cell Biol. 113, 1213 (1991). Alternatively or in addition, adherence to cells expressing the respective receptor can be used to assay ligand binding. For example, EL-4 cells (ATCC TIB39) are known to express high levels of L-selectin on their surfaces, and can therefore be used in cell adhesion assays for L-selectin ligands. Adherent cells can be quantitated by lactate dehydrogenase activity [Bradley et al., J. Cell. Biol. 105, 991 (1987)].

The terms "nucleic acid molecule encoding", "DNA sequence encoding" and "DNA encoding" refer to the order or sequence of deoxyribonucleotides along a strand of deoxyribonucleic acid. The order of these deoxyribonucleotides determines the order of amino acids along the polypeptide chain. The DNA sequence thus codes for the amino acid sequence.

The term "isolated" when used in relation to a nucleic acid or a protein refers to a nucleic acid or protein that is identified and separated from at least one containment nucleic acid or protein with which it is ordinarily associated in its natural source. Isolated nucleic acid or protein is such present in a form or setting that is different from that in which it is found in nature. However, isolated nucleic acid encoding a selectin ligand includes such nucleic acid in cells ordinarily expressing selectin ligands where the nucleic acid is in a chromosomal location different from that of natural cells, or is otherwise flanked by a different DNA sequence than that found in nature.

"Low stringency conditions" are overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextrane sulfate, and 20 µg/ml denatured, sheared salmon sperm DNA, followed by washing the filters in 1x SSC at about 50° C.

Nucleic acid is "operably linked" when it is placed into a functional relationship with another nucleic acid sequence. For example, DNA for a presequence or secretory leader is operably linked to a DNA encoding a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, then synthetic oligonucleotide adaptors or linkers are used in accord with conventional practice.

The terms "replicable expression vehicle" and "expression vehicle" refer to a piece of DNA, usually double-stranded, which may have inserted into it a piece of foreign DNA. Foreign DNA is defined as heterologous DNA, which is DNA not naturally found in the host cell. The vehicle is used to transport the foreign or heterologous DNA into a suitable host cell. Once in the host cell, the vehicle can replicate independently of the host chromosomal DNA, and several copies of the vehicle and its inserted (foreign) DNA may be generated. In addition, the vehicle contains the necessary elements that permit translating the foreign DNA into a polypeptide. Many molecules of the polypeptide encoded by the foreign DNA can thus be rapidly synthesized.

In the context of the present invention the expressions "cell" "cell line" and "cell culture" are used interchangeably, and all such designations include progeny. It is also understood that all progeny may not be precisely identical in DNA content, due to deliberate or inadvertent mutations. Mutant progeny that have the same function or biological property as screened for in the originally transformed cell are included.

The terms "transformed host cell" and "transformed" refer to the introduction of DNA into a cell. The cell is termed a "host cell" and it may be a prokaryotic or a eukaryotic cell. Typical prokaryotic host cells include various strains of E. Coli. Typical eukaryotic host cells are mammalian, such as Chinese hamster ovary cells or human embryonic kidney 293 cells. The introduced DNA is usually in the form of a vector containing an inserted piece of DNA. The introduced DNA sequence may be from the same species as the host cell or a different species from the host cell, or it may be a hybrid DNA sequence, containing some foreign and some homologous DNA.

"Ligation" refers to a process of forming phosphodiester bonds between two nucleic acid fragments. To ligate the DNA fragments together, their ends must be compatible. In some cases, the ends will be directly compatible after endonuclease digestion. However, it may be necessary to first convert the staggered ends commonly produced after endonuclease digestion to blunt ends to make them compatible for ligation. To blunt ends, the DNA is treated in a suitable buffer for at least 15 minutes at 15° C. with about 10 units of the Klenow fragment of DNA polymerase I or T4 DNA polymerase in the presence of the four deoxyribonucleotide triphosphates. The DNA is then purified by phenol-chloroformextraction and ethanol precipitation. The DNA fragments that are to be ligated together are put in solution in about equimolar amounts. The solution will also contain ATP, ligase buffer, and a ligase such as T4 DNA ligase at about 10 units per 0.5 µg of DNA. If the DNA is to be ligated into a vector, the vector is first linearized by digestion with the appropriate restriction endonuclease(s). The linearized fragment is then treated with bacterial alkaline phosphatase, or calf intestinal phosphatase to prevent self-ligation during the ligation step.

The terms "amino acid" and "amino acids" refer to all naturally occurring L-α-amino acids. This definition is meant to include norleucine, ornithine, and homocysteine. The amino acids are identified by either the single-letter or three-letter designations:

| Asp | D | aspartic acid |
|-----|---|---------------|
| Thr | T | threonine |
| Ser | S | serine |
| Glu | E | glutamic acid |
| Pro | P | proline |
| Gly | G | glycine |
| Ala | A | alanine |
| Cys | C | cysteine |
| Val | V | valine |
| Met | M | methionine |
| Ile | I | isoleucine |
| Leu | L | leucine |
| Tyr | Y | tyrosine |
| Phe | F | phenylalanine |
| His | H | histidine |
| Lys | K | lysine |
| -continued | | |
| Arg | R | arginine |
| Trp | W | tryptophan |
| Gln | Q | glutamine |
| Asn | N | asparagine |

These amino acids may be classified according to the chemical composition and properties of their side chains. They are broadly classified into two groups, charged and uncharged. Each of these groups is divided into subgroups to classify the amino acids more accurately:

I. Charged Amino Acids

Acidic Residues: aspartic acid, glutamic acid

Basic Residues: lysine, arginine, histidine

II. Uncharged Amino Acids

Hydrophilic Residues: serine, threonine, asparagine, glutamine

Aliphatic Residues: glycine, alanine, valine, leucine, isoleucine

Non-polar Residues: cysteine, methionine, proline

Aromatic Residues: phenylalanine, tyrosine, tryptophan

The terms "alteration", "amino acid sequence alteration", "variant" and "amino acid sequence variant" refer to molecules with some differences in their amino acid sequences as compared to the native sequence of a selectin, e.g. an L-selectin ligand. Ordinarily, the variants will possess at least 70% homology with a native selectin ligand, and preferably, they will be at least about 80%, more preferably at least about 90% homologous with a native selectin ligand. The amino acid sequence variants falling within this invention possess substitutions, deletions, and/or insertions at certain within the amino acid sequence of a native selectin ligand.

Substitutional variants are those that have at least one amino acid residue in a native sequence removed and a different amino acid inserted in its place at the same position. The substitutions may be single, where only one amino acid in the molecule has been substituted, or they may be multiple, where two or more amino acids have been substituted in the same molecule.

Substantial changes in the properties of the ligand may be obtained by substituting an amino acid with a side chain that is significantly different in charge and/or structure from that of the native amino acid. This type of substitution would be expected to affect the structure of the polypeptide backbone and/or the charge or hydrophobicity of the molecule in the area of the substitution.

Moderate changes in the ligand properties would be expected by substituting an amino acid with a side chain that is similar in charge and/or structure to that of the native molecule. This type of substitution, referred to as a conservative substitution, would not be expected to substantially alter either the structure of the polypeptide backbone or the charge or hydrophobicity of the molecule in the area of the substitution.

Insertional variants are those with one or more amino acids inserted immediately adjacent to an amino acid at a particular position in a native selectin ligand sequence. Immediately adjacent to an amino acid means connected to either the α-carboxy or α-amino functional group of the amino acid. The insertion may be one or more amino acids. Ordinarily, the insertion will consist of one or two conservative amino acids. Amino acids similar in charge and/or structure to the amino acids adjacent to the site of insertion are defined as conservative. Alternatively, this invention includes insertion of an amino acid with a charge and/or structure that is substantially different from the amino acids adjacent to the site of insertion.

Deletional variants are those with one or more amino acids in the native selectin ligand amino acid sequence removed. Ordinarily, deletional variants will have one or two amino acids deleted in a particular region of the molecule.

An essential role of the protein core of the present selectin ligands is to present the specific carbohydrate structure recognized by a selectin receptor to the respective receptor.

Accordingly, any alteration within the two highly O-glycosylated, serine- and threonine-rich regions (amino acids 42–63 and amino acids 93–122 in FIG. 4) of the L-selectin ligand amino acid sequence is expected to have more significant effect on the lymphocyte-high endothelial venule interaction than changes in other regions of the protein. As it will be shown hereinbelow, the highly O-glycosylated regions are essential to provide a rigid, inflexible "bottle brush" structure that allows for the large number of O-linked carbohydrate ligands attached to the serine and threonine residues to be appropriately presented to the leukocyte surface-localized L-selectin lectin domains, thereby mediating the carbohydrate-dependent adhesive interaction. Alterations within these regions are expected to result in molecules the receptor binding activities of which will be significantly different from that of the corresponding native ligand.

The glycoprotein ligands of the present invention comprise fucose, sialic acid and an anionic component, preferably sulfate esters as O-linked carbohydrate components, and it is believed that fucose, like sialic acid, and sulfate are required for full ligand activity.

The carbohydrate component of the present glycoprotein ligands preferably has a structure similar to those disclosed in copending application Ser. No. 07/800,923 filed 27 Nov. 1991, the content of which is hereby expressly incorporated by reference. Glycosylation variants retaining the qualitative selectin binding activity of the ligands of the present invention are also within the scope herein.

Examples of specific carbohydrate components of the glycoprotein ligands of the invention can be expressed as follows:

NeuNAcα2–3Galβ1–4(Fucα1–3)GlcNAc
NeuNAcA2–3Galβ1–4GlcNAcB1–3GalB1–4(FucA1–4(FucA1–3)GlcNAc.

"Northern blot analysis" is a method used to identify RNA sequences that hybridize to a known probe such as an oligonucleotides, DNA fragment, cDNA or fragment thereof, or RNA fragment. The probe is labeled with a radioisotope such as $^{32}P$, or by biotinylation, or with an enzyme. The RNA to be analyzed is usually electrophoretically separated on an agarose or polyacrylamide gel, transferred to nitrocellulose, nylon, or other suitable membrane, and hybridized with the probe, using standard techniques well known in the art such as those described in sections 7.39–7.52 of Sambrook et al., Molecular Cloning: A Laboratory Manual, New York: Cold Spring Harbor Laboratory Press, 1989.

"Oligonucleotides" are short-length, single- or double-stranded polydeoxynucleotides that are chemically synthesized by known methods [such as phosphotriester, phosphite, or phosphoramidite chemistry, using solid phase techniques such as those described in EP 266,032, published 4 May 1988, or via deoxynucleoside H-phosphanate intermediates as described by Froehler et al., Nucl. Acids Res. 14, 5399 (1986)]. They are then purified on polyacrylamide gels.

The technique of "polymerase chain reaction" or "PCR", as used herein, generally refers to a procedure wherein minute amounts of a specific piece of nucleic acid, RNA and/or DNA, are amplified as described in U.S. Pat. No. 4,683,195, issued 28 Jul. 1987 and in Current Protocols in Molecular Biology, Ausubel et al. eds., Greene Publishing Associates and Wiley-Interscience 1991, Volume 2, Chapter 15.

"Transformation" means introducing DNA into an organism so that the DNA is replicable, either as an extrachromosomal element or by chromosomal integration.

"Transfection" refers to the taking up of an expression vector by a host cell whether or not any coding sequences are in fact expressed.

The terms "treatment", "treating" and grammatical variants thereof, are used in the broadest sense and include prevention and amelioration of certain undesired symptoms or conditions.

"Gas phase microsequencing" was accomplished based upon the following procedures. The purified protein was either sequenced directly by automated Edman degradation with a model 470A Applied Biosystems gas phase sequencer equipped with a 120A PTH amino acid analyzer or sequenced after digestion with various chemicals or enzymes. PTH amino acids were integrated using a ChromPerfect data system (Justice Innovations, Palo Alto, Calif.). Sequence interpretation was performed on a VAX 11/785 Digital Equipment Corporation computer as described by Menzel et al., J. Chromatography 404, 41 (1987). In some cases, aliquots of the MPLC fractions are electrophoresed on 5–20% SDS polyacrylamide gels, electrotransferred to a PVDF membrane (ProBlott, ABI, Foster City, Calif.) and stained with Coomassie Brilliant Blue [Matsudaira, P. J., Biol. Chem. 262, 10035 (1987)]. The specific protein was excised from the blot for N-terminal sequencing. To determine internal protein sequences, HPLC fractions were dried under vacuum (SpeedVac), resuspended in appropriate buffers, and digested with cyanogen bromide, the lysine-specific enzyme Lys-C (Wako Chemicals, Richmond, Va.) or Asp-N (Boehringer Mannhelm, Indianapolis, Ind.). After digestion, the resultant peptides were sequenced as a mixture or were resolved by HPLC on a C4 column developed with a propanol gradient in 0.1% TFA before sequencing as described above.

The term "monoclonal antibody" as used herein refers to an antibody obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

The monoclonal antibodies included within the scope of the invention include hybrid and recombinant antibodies produced by splicing a variable (including hypervariable) domain of an anti-selectin ligand antibody with a constant domain (e.g. "humanized" antibodies), only one of which is directed against a selectin ligand, or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$, and Fv). Cabilly, et al., U.S. Pat. No. 4,816,567; Mage & Lamoyi, in Monoclonal Antibody Production Techniques and Applications, pp.79–97 (Marcel Dekker, Inc., New York, 1987).

Thus, the modifier "monoclonal" indicates the character of the antibody as being obtained from such a substantially homogeneous population of antibodies, and is not to be construed as requiring production of the antibody by any particular method.

II. GENERAL METHODS

A. Obtaining DNA Encoding A Selectin Ligand

The DNA encoding a selectin ligand may be obtained from any cDNA library prepared from tissue believed to possess mRNA for the selectin ligand and to express it at a detectable level. An L-selectin ligand gene thus may be obtained from a cDNA library prepared from (mesenteric or peripheral) lymph nodes. Genes encoding the other selectin ligands can be prepared from other cDNA libraries in an analogous manner.

Libraries are screened with probes designed to identify the gene of interest or the protein encoded by it. For cDNA expression libraries, suitable probes usually include mono- and polyclonal antibodies that recognize and specifically bind to the desired protein; oligonucleotides of about 20–80 bases in length that encode known or suspected portions of the selectin ligand cDNA from the same or different species; and/or complementary or homologous cDNAs or their fragments that encode the same or similar gene.

An alternative means to isolate the gene encoding a selectin ligand, e.g. an L-selectin ligand, is to use polymerase chain reaction (PCR) methodology as described in section 14 of Sambrook et al., Supra or in Chapter 15 of Current protocols in Molecular Biology, Supra.

Another alternative is to chemically synthesize the gene encoding the desired selectin ligand using one of the methods described in Engels et al., Agnew. Chem. Int. Ed. Engl. 28, 716 (1989). These methods include triester, phosphite, phosphoramidite and H-Phosphonate methods, PCR and other autoprimer methods, and oligonucleotide syntheses on solid supports. These methods may be used if the entire nucleic acid sequence of the gene is known, or the sequence of the nucleic acid complementary to the coding strand is available, or, alternatively, if the target amino acid sequence is known, one may infer potential nucleic acid sequences, using known and preferred coding residues for each amino acid residue.

A preferred method for practicing this invention is to use carefully selected oligonucleotide sequences to screen cDNA libraries from various tissues, preferably mammalian lymph node high endothelial venules (L-selectin ligand), or myeloid cells (E-selectin and P-selectin ligands). Among the preferred mammals are humans and members of the following orders: bovine, ovine, equine, murine, and rodentia.

The oligonucleotide sequences selected as probes should be of sufficient length and sufficiently unambiguous that false positives are minimized. The actual nucleotide sequence(s) is/are usually based on conserved or highly homologous nucleotide sequences or regions of a selectin ligand, e.g. L-selectin ligand.

The DNA shown in FIG. 4 (SEQ. ID. No.:2) may be used to isolate DNA encoding other selectin ligands or to isolate DNA encoding L-selectin ligand from another animal species via hybridization employing the methods discussed above. The preferred animals are mammals, particularly human, bovine, ovine, equine, feline, canine and rodentia, and more specifically human, bovine, rats, and rabbits.

B. Construction Of Amino Acid Sequence Variants

The amino acid sequence variants of the selectin ligands of this invention are preferably constructed by mutating the DNA sequence that encodes the protein core of a wild-type selectin, e.g. L-selectin ligand. Generally, particular regions or sites of the DNA will be targeted for mutagenesis, and thus the general methodology employed to accomplish this is termed site-directed mutagenesis. The mutations are made using DNA modifying enzymes such as restriction endonucleases (which cleave DNA at particular locations), nucleases (which degrade DNA) and/or polymerases (which synthesize DNA).

1. Simple Deletions and Insertions

Restriction endonuclease digestion of DNA followed by ligation may be used to generate deletions, as described in section 15.3 of Sambrook et al., Supra. To use this method, it is preferable that the foreign DNA be inserted into a plasmid vector. A restriction map of both the foreign (inserted) DNA and the vector DNA must be available, or the sequence of the foreign DNA and the vector DNA must be known. The foreign DNA must have unique restriction sites that are not present in the vector. Deletions are then made in the foreign DNA by digesting it between these unique restriction sites, using the appropriate restriction endonucleases under conditions suggested by the manufacturer of the enzymes. If the restriction enzymes used create blunt ends or compatible ends, the ends can be directly ligated together using a ligase such as bacteriophage T4 DNA ligase and incubating the mixture at 16° C. for 1–4 hours in the presence of ATP and ligase buffer as described in section 1.68 of Sambrook et al., Supra. If the ends are not compatible, they must first be made blunt by using the Klenow fragment of DNA polymerase I or bacteriophage T4 DNA polymerase, both of which require the four deoxyribonucleotide triphosphates to fill-in the overhanging single-stranded ends of the digested DNA. Alternatively, the ends may be blunted using a nuclease such as nuclease S1 or mung-bean nuclease, both of which function by cutting back the overhanging single strands of DNA. The DNA is then religated using a ligase. The resulting molecule is a deletion variant.

A similar strategy may be used to construct insertion variants, as described in section 15.3 of Sambrook et al., Supra. After digestion of the foreign DNA at the unique restriction site(s), an oligonucleotide is ligated into the site where the foreign DNA has been cut. The oligonucleotide is designed to code for the desired amino acids to be inserted and additionally has 5' and 3' ends that are compatible with the ends of the foreign DNA that have been digested, such that direct ligation is possible.

2. Oligonucleotide-Mediated Mutagenesis

Oligonucleotide-directed mutagenesis is the preferred method for preparing the substitution variants of this invention. It may also be used to conveniently prepare the deletion and insertion variants of this invention. This technique is well known in the art as described by Adelman et al. (DNA, 2:183 [1983]).

Generally, oligonucleotides of at least 25 nucleotides in length are used to insert, delete or substitute two or more nucleotides in the selectin ligand molecule. An optimal oligonucleotide will have 12 to 15 perfectly matched nucleotides on either side of the nucleotides coding for the mutation. This ensures that the oligonucleotide will hybridize properly to the single-stranded DNA template molecule. The oligonucleotides are readily synthesized using techniques well known in the art such as that described by Crea et al. (Proc. Nat'l. Acad. Sci. USA, 75:5765 [1978]).

The DNA template molecule is the single-stranded form of the vector with its wild-type cDNA selectin ligand insert. The single-stranded template can only be generated by those vectors that are either derived from bacteriophage M13 vectors (the commercially available M13mp18 and M13mp19 vectors are suitable), or those vectors that contain a single-stranded phage origin of replication as described by Veira et al. (Meth. Enzymol., 153:3 [1987]). Thus, the cDNA selectin ligand that is to be mutated must be inserted into one of these vectors in order to generate single-stranded template. Production of the single-stranded template is described in sections 4.21–4.41 of Sambrook et al., Supra.

To mutagenize the native selectin ligand sequence, the oligonucleotide is annealed to the single-stranded DNA template molecule under suitable hybridization conditions. A DNA polymerizing enzyme, usually the Klenow fragment of E. coli DNA polymerase I, is then added. This enzyme uses the oligonucleotide as a primer to complete the synthesis of the mutation-bearing strand of DNA. Thus, a heteroduplex molecule is formed such that one strand of DNA encodes the native selectin ligand inserted in the vector, and the second strand of DNA encodes the mutated form of the selectin ligand inserted into the same vector. This heteroduplex molecule is then transformed into a suitable host cell, usually a prokaryote such as E. coli JM101. After growing the cells, they are plated on to agarose plates and screened using the oligonucleotide primer radiolabeled with 32-P to identify the colonies that contain the selectin ligand mutated in its protein core. These colonies are selected, and the DNA is sequenced to confirm the presence of mutations in the protein core of the molecule.

Mutants with more than one amino acid substituted may be generated in one of several ways. If the amino acids are located close together in the polypeptide chain, they may be mutated simultaneously using one oligonucleotide that codes for all of the desired amino acid substitutions. If, however, the amino acids are located some distance from each other (separated by more than ten amino acids, for example) it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. The alternative method involves two or more rounds of mutagenesis to produce the desired mutant. The first round is as described for the single mutants DNA encoding the protein core of a native selectin ligand is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

3. PCR Mutagenesis

PCR mutagenesis is also suitable for making amino acid variants of the selectin ligands of the present invention. While the following discussion refers to DNA, it is understood that the technique also find application with RNA. The PCR technique generally refers to the following procedure. When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers is designed to overlap the position of the mutation and to contain the mutation; the sequence of the other primer must be identical to a stretch of sequence of the opposite strand of the plasmid, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone.

If the ratio of template to product material is extremely low, the vast majority of product DNA fragments incorporate the desired mutation(s). This product material is used to replace the corresponding region in the plasmid that served as PCR template using standard DNA technology. Mutations at separate positions can be introduced simultaneously by either using a mutant second primer or performing a second PCR with different mutant primers and ligating the two resulting PCR fragments simultaneously to the vector fragment in a three (or more)-part ligation.

C. Insertion Of DNA Into A Replicable Vector

The cDNA or genomic DNA encoding the (native or variant) selectin ligands of the present invention is inserted into a replicable vector for further cloning or expression. Many vectors are available, and selection of the appropriate vector will depend on 1) whether it is to be used for DNA amplification (cloning) or for expression, 2) the size of the DNA to be inserted into the vector, and 3) the host cell to be transformed with the vector. Each vector contains various components depending on its function and the host cell with which it is compatible. The vector components generally include, but are not limited to, one or more of the following: a signal sequence, an origin of replication, one or more marker genes, an enhancer element, a promoter and a transcription terminator sequence. Specific vectors will be discussed hereinbelow in conjunction with the host cells with which they are compatible.

Suitable vectors are prepared using standard recombinant DNA procedures. Isolated plasmids and DNA fragments are cleaved, tailored, and ligated together in a specific order to generate the desired vectors.

The DNA is cleaved using the appropriate restriction enzyme or enzymes in a suitable buffer. In general, about 0.2–1 μg of plasmid or DNA fragments is used with about 1–2 units of the appropriate restriction enzyme in about 20 μl of buffer solution. (Appropriate buffers, DNA concentrations, and incubation times and temperatures are specified by the manufacturers of the restriction enzymes.) Generally, incubation times of about one or two hours at 37° C. are adequate, although several enzymes require higher temperatures. After incubation, the enzymes and other contaminants are removed by extraction of the digestion solution with a mixture of phenol and chloroform, and the DNA is recovered from the aqueous fraction by precipitation with ethanol.

To ligate the DNA fragments together to form a functional vector, the ends of the DNA fragments must be compatible with each other. In some cases the ends will be directly compatible after endonuclease digestion. However, it may be necessary to first convert the sticky ends, commonly produced by endonuclease digestion, to blunt ends to make them compatible for ligation. To blunt the ends, the DNA is treated in a suitable buffer for at least 15 minutes at 15° C. with 10 units of the Klenow fragment of DNA Polymerase I (Klenow) in the presence of the four deoxynucleotide triphosphates. It is then purified by phenolchloroform extraction and ethanol precipitation.

The cleaved DNA fragments may be size-separated and selected using DNA gel electrophoresis. The DNA may be electrophoresed through either an agarose or a polyacrylamide matrix. The selection of the matrix will depend on the size of the DNA fragments to be separated. After electrophoresis, the DNA is extracted from the matrix by electroelution, or, if low-melting agarose has been used as the matrix, by melting the agarose and extracting the DNA from it, as described in sections 6.30–6.33 of Sambrook et al., Supra.

The DNA fragments that are to be ligated together (previously digested with the appropriate restriction enzymes such that the ends of each fragment to be ligated are compatible) are present in solution in about equimolar amounts. The solution will also contain ATP, ligase buffer and a ligase such as T4 DNA ligase at about 10 units per 0.5 µg of DNA. If the DNA fragment is to be ligated into a vector, the vector is first linearized by cutting with the appropriate restriction endonuclease(s) and then phosphatased with either bacterial alkaline phosphatase or calf intestinal alkaline phosphatase. This prevents self-ligation of the vector during the ligation step.

After ligation, the vector with the foreign gone now inserted is transformed into a suitable host cell. The transformed cells are selected by growth on an antibiotic, commonly tetracycline (tet) or ampicillin (amp), to which they are rendered resistant due to the presence of tet and/or amp resistance genes on the vector. If the ligation mixture has been transformed into a eukaryotic host cell, transformed cells may be selected by the DHFR/MTX system described above. The transformed cells are grown in culture and the plasmid DNA (plasmid refers to the vector ligated to the foreign gene of interest) is then isolated. This plasmid DNA is then analyzed by restriction mapping and/or DNA sequencing. DNA sequencing is generally performed by either the method of Messing et al., Nucleic Acids Res., 9:309 (1981) or by the method of Maxam et al., Methods of Enzymology, 65:499 (1980).

D. Selection And Transformation Of Host Cells

The carbohydrate component of the glycoprotein ligands of the present invention is essential for receptor recognition and receptor binding. Accordingly, eukaryotic host cells expressing proteins in a glycosylated form are preferred for the expression of the ligands herein. However, expression in prokaryotes which do not glycosylate proteins, such as E. coli is also feasible. The unglycosylated protein can subsequently be glycosylated, e.g. by chemical and/or enzymatic methods detailed hereinbelow.

1. Eukaryotic Multicellular Organisms

Multicellular organisms are preferred as hosts to practice this invention. While both invertebrate and vertebrate cell cultures are acceptable, vertebrate cell cultures, particularly mammalian cultures, are preferable. Examples of suitable cell lines include monkey kidney CVI line transformed by SV40 (COS-7, ATCC CRL 1651); human embryonic kidney line 293S (Graham et al., J. Gen. Virol., 36:59 [1977]); baby hamster kidney cells (BHK, ATCC CCL 10); Chinese hamster ovary cells (Urlab and Chasin, Proc. Natl, Acad. Sci USA, 77:4216 [1980]); mouse sertoli cells (TM4, Mather, Biol. Reprod., 23:243 [1980]); monkey kidney cells (CVI-76, ATCC CCL 70); African green monkey kidney cells (VERO- 76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor cells (MMT 060562, ATCC CCL 51); rat hepatoma cells (HTC, MI.54, Baumann et al., J. Cell Biol., 85:1 [1980]); and TRI cells (Mather et al., Annals N.Y. Acad. Sci., 383:44 [1982]). Expression vectors for these cells ordinarily include (if necessary) DNA sequences for an origin of replication, a promoter located in front of the gene to be expressed, a ribosome binding site, an RNA splice site, a polyadenylation site, and a transcription terminator site.

Promoters used in mammalian expression vectors are often of viral origin. These vital promoters are commonly derived from polyoma virus, Adenovirus2, and most frequently Simian Virus 40 (SV40). The SV40 virus contains two promoters that are termed the early and late promoters. These promoters are particularly useful because they are both easily obtained from the virus as one DNA fragment that also contains the vital origin of replication (Fiers et al., Nature, 273:113 [1978]). Smaller or larger SV40 DNA fragments may also used, provided they contain the approximately 250-bp sequence extending from the HindIII site toward the BglI site located in the viral origin of replication.

Alternatively, promoters that are naturally associated with the foreign gene (homologous promoters) may be used provided that they are compatible with the host cell line selected for transformation.

An origin of replication may be obtained from an exogenous source, such as SV40 or other virus (e.g., Polyoma, Adeno, VSV, BPV) and inserted into the cloning vector. Alternatively, the origin of replication may be provided by the host cell chromosomal replication mechanism. If the vector containing the foreign gene is integrated into the host cell chromosome, the latter is often sufficient.

Satisfactory amounts of selectin ligand can be produced by transformed cell cultures. However, the use of a secondary DNA coding sequence can enhance production levels. The secondary coding sequence typically comprises the enzyme dihydrofolate reductase (DHFR). The wild-type form of DHFR is normally inhibited by the chemical methotrexate (MTX). The level of DHFR expression in a cell will vary depending on the amount of MTX added to the cultured host cells. An additional feature of DHFR that makes it particularly useful as a secondary sequence is that it can be used as a selection marker to identify transformed cells.

Two forms of DHFR are available for use as secondary sequences, wild-type DHFR and MTX-resistant DHFR. The type of DHFR used in a particular host cell depends on whether the host cell is DHFR deficient (such that it either produces very low levels of DHFR endogenously, or it does not produce functional DHFR at all). DHFR-deficient cell lines such as the Clio cell line described by Urlaub and Chasin (Proc. Natl. Acad., Sci. (USA) 77:4216 [1980]) are transformed with wild-type DHFR coding sequences. After transformation, these DHFR-deficient cell lines express functional DHFR and are capable of growing in a culture medium lacking the nutrients hypoxanthine, glycine and thymidine. Nontransformed cells will not survive in this medium.

The MTX-resistant form of DHFR can be used as a means of selecting for transformed host cells in those host cells that endogenously produce normal amounts of functional DHFR that is MTX sensitive. The CHO-K1 cell line (ATCC number CL 61) possesses these characteristics, and is thus a useful cell line for this purpose. The addition of MTX to the cell culture medium will permit only those cells transformed with the DNA encoding the MTX-resistant DHFR to grow. The nontransformed cells will be unable to survive in this medium.

The mammalian host cells used to produce the variants of this invention may be cultured in a variety of media. Commercially available media such as Ham's F10 (Sigma), Minimal Essential Medium ([MEM], Sigma), RPMI-1640 (Sigma), and Dulbecco's Modified Eagle's Medium ([DMEM], Sigma) are suitable for culturing the host cells. Any of these media may be supplemented as necessary with hormones and/or other growth factors (such as insulin, transfertin, or epidermal growth factor), salts (such as sodium chloride, calcium, magnesium, and phosphate), buffers (such as HEPES), nucleosides (such as adenosine and thymidine), antibiotics (such as Gentamycin), trace elements (defined as inorganic compounds usually present at final concentrations in the micromolar range), and glucose or an equivalent energy source. Any other necessary supplements may also be included at appropriate concentrations that would be known to those skilled in the art.

2. Eukaryotic Microbes

In addition to multicellular eukaryotes, eukaryotic microbes such as filamentous fungi or yeast are suitable to practice this invention. Saccharomyes cerevisiae, or common baker's yeast, is the most commonly used among lower eukaryotic host microorganisms. However, a number of other genera, species, and strains are commonly available and useful herein, such as Schizosaccharomyces pombe [Beach and Nurse, Nature, 290:140 (1981); EP 139,383 published May 2, 1985]; Kluyveromyces hosts (U.S. 4,943,529; Fleer et al., Supra) such as, e.g., K. lactis [MW98-8C, CBS683, CBS4574; Louvencourt et al., J. Bacteriol., 737 (1983) ], K. fragilis (ATCC 12,424), K. bulgaricus (ATCC 16,045), K. wickermii (ATCC 24,178); K. waltii (ATCC 56,500), K. drosophilarum (ATCC 36,906; Van den Berg et al., Supra), K. thermotolerans, and K. marxianus; yarrowia [EP 402,226]; Pichia pastoris [EP 183,070; Sreekrishna et al., J. Basic Microbiol., 28:265–278 (1988)]; Trichoderma reesia [EP 244,234]; Neurospora crassa [Case et al., Proc. Natl. Acad. Sci. USA, 76:5259 (1979)]; Schwanniomyces such as Schwanniomyces occidentalis [EP 394,538 published 31 Oct. 1990]; and filamentous fungi such as, e.g., Neurospora, Penicillium, Tolypocladium [WO 91/00357 published 10 Jan. 1991], and Aspergillus hosts such as A. nidulans [Ballance et al., Biochem. Biophys. Res. Commun., 112:284 (1983); Tilburn et al., Gene, 26:205 (1983); Yelton et al., Proc. Natl. Acad. Sci. USA, 81:1470 (1984)] and A. niger [Kelly and Hynes, EMBO J., 4:475 (1985)].

Suitable promoting sequences in yeast vectors include the promoters for 3-phosphoglycerate kinase (Hitzeman et al., J. Biol. Chem., 255:2073 [1980]) or other glycolytic enzymes (Hess et al., J. Adv. Enzyme Reg., 7:149 [1968]; Holland et al., Biochemistry, 17:4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In the construction of suitable expression plasmids, the termination sequences associated with these genes are also ligated into the expression vector 3') of the sequence desired to be expressed to provide polyadenylation of the mRNA and termination. Other promoters that have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

3. Prokaryotic Cells

Prokaryotes are particularly useful for rapid production of large amounts of DNA, for production of single-stranded DNA templates used for site-directed mutagenesis, for screening many mutants simultaneously, and for DNA sequencing of the mutants generated. Suitable prokaryotic host cells include strain 294 (ATCC number 31,446), E. coli strain W3110 (ATCC number 27,325) E. coli X1776 (ATCC number 31,537), and E. coli B; however many other strains of E. coli, such as HB101, JM101, NM522, NM538, NM539, and many other species and genera of prokaryotes may be used as well.

Prokaryotes may also be used as hosts for expression of DNA sequences. The E. coli strains listed above, bacilli such as Bacillus subtilis, other enterobacteriaceae such as Salmonella typhimurium or Serratia marcesans, and various Pseudomonas species may all be used as hosts.

Plasmid vectors containing replicon and control sequences that are derived from species compatible with the host cell are used with these hosts. The vector usually has a replication site, marker genes that provide phenotypic selection in transformed cells, one or more promoters, and a polylinker region containing several restriction sites for insertion of foreign DNA. Plasmids typically used for transformation of E. coli include pBR322, pUC18, pUC19, pUC118, pUC119, and Bluescript M13, all of which are described in sections 1.12–1.20 of Sambrook et al., Supra. However, many other suitable vectors are available as well. These vectors contain genes coding for ampicillin and/or tetracycline resistance which enables cells transformed with these vectors to grow in the presence of these antibiotics. D The promoters most commonly used in prokaryotic vectors include the β-lactamase (penicillinase) and lactose promoter systems (Chang et al. Nature, 375:615 [1978]; Itakura et al., Science, 198:1056 [1977]; Goeddel et al., Nature, 281:544 [1979]) and a tryptophan (trp) promoter system (Goeddel et al., Nucl. Acids Res., 8:4057 [1980]; EPO Appl. Publ. No. 36,776), and the alkaline phosphatase systems. While these are the most commonly used, other microbial promoters have been utilized, and details concerning their nucleotide sequences have been published, enabling a skilled worker to ligate them functionally into plasmid vectors (see Siebenlist et al., Cell, 20:269 [1980]).

4. Secretion Systems

Many eukaryotic proteins normally secreted from the cell contain an endogenous signal sequence as part of the amino acid sequence. This sequence targets the protein for export from the cell via the endoplasmic reticulum and Golgi apparatus. The signal sequence is typically located at the amino terminus of the protein, and ranges in length from about 13 to about 36 amino acids. Although the actual sequence varies among proteins, all known eukaryotic signal sequences contain at least one positively charged residue and a highly hydrophobic stretch of 10–15 amino acids (usually rich in the amino acids leucine, isoleucine, alanine, valine and phenylalanine) near the center of the signal sequence. The signal sequence is normally absent from the secreted form of the protein, as it is cleaved by a signal peptidase located on the endoplasmic reticulum during translocation of the protein into the endoplasmic reticulum. The protein with its signal sequence still attached is often referred to as the 'pre-protein' or the immature form of the protein.

However, not all secreted proteins contain an amino terminal signal sequence that is cleaved. Some proteins, such as ovalbumin, contain a signal sequence that is located on an internal region of the protein. This sequence is not normally cleaved during translocation.

Proteins normally found in the cytoplasm can be targeted for secretion by linking a signal sequence to the protein. This is readily accomplished by ligating DNA encoding a signal sequence to the 5' end of the DNA encoding the protein and then expressing this fusion protein in an appropriate host cell. The DNA encoding the signal sequence may be obtained as a restriction fragment from any gene encoding a protein with a signal sequence. Thus, prokaryotic, yeast, and eukaryotic signal sequences may be used herein, depending on the type of host cell utilized to practice the invention. The DNA encoding the signal sequence portion of the gene is excised using appropriate restriction endonucleases and then ligated to the DNA encoding the protein to be secreted.

Selection of a functional signal sequence requires that the signal sequence is recognized by the host cell signal peptidase such that cleavage of that signal sequence and secretion of the protein will occur. The DNA and amino acid sequence encoding the signal sequence portion of several eukaryotic genes including, for example, human growth hormone, proinsulin, and proalbumin are known (see Stryer, Biochemistry, W. H. Freeman and Company, New York [1988], p. 769) and can be used as signal sequences in appropriate eukaryotic host cells. Yeast signal sequences, as for example acid phosphatase (Arima et al., Nuc. Acids Res., 11:1657 [1983]), alpha-factor, alkaline phosphatase and invertase may be used to direct secretion from yeast host cells. Prokaryotic signal sequences from genes encoding, for example, Lamb or OmpF (Wong et al., Gene 68:193 1988]), MalE, PhoA, or beta-lactamase, as well as other genes, may be used to target proteins from prokaryotic cells into the culture medium.

An alternative technique to provide a protein of interest with a signal sequence such that it may be secreted is to chemically synthesize the DNA encoding the signal sequence. In this method, both strands of an oligonucleotide encoding the selected signal sequence are chemically synthesized and then annealed to each other to form a duplex. The double-stranded oligonucleotide is then ligated to the 5' end of the DNA encoding the protein.

The construct containing the DNA encoding the protein with the signal sequence ligated to it can then be ligated into a suitable expression vector. This expression vector is transformed into an appropriate host cell and the protein of interest is expressed and secreted.

E. Transformation Methods

Cultures of mammalian host cells and other host cells that do not have rigid cell membrane barriers are usually transformed using the calcium phosphate method as originally described by Graham and Van der Eb (Virology, 52:546 [1978]) and modified as described in sections 16.32–16.37 of Sambrook et al. Supra. However, other methods for introducing DNA into cells such as Polybrene (Kawai and Nishizawa, Mol. Cell. Biol., 4:1172 [1984]), protoplast fusion (Schaffner, Proc. Natl. Acad. Sci, USA, 77:2163 [1980]), electroporation (Neumann et al., EMBO J., 1:841 [1982]), and direct microinjection into nuclei (Capecchi, Cell, 22:479 [1980]) may also be used.

Yeast host cells are generally transformed using the polyethylene glycol method, as described by Hinnen (Proc. Natl. Acad. Sci. U.S.A., 75:1929 [1978]).

F. Culturing The Host Cells

The mammalian host cells used to produce the selectin ligands of the present invention may be cultured in a variety of media. Commercially available media, such as Ham's F10 (Sigma), Minimal Essential Medium (MEM, Sigma), RPMI-1640 (sigma), or Dulbecco's Modified Eagle's Medium (DMEM, Sigma) are suitable for culturing such host cells. In addition, any of the media described in Ham and Wallace, Meth. Enz. 58, 44 (1979); Barnes and Sato, Anal. Biochem. 102, 255 (1980); U.S. Pat. Nos. 4,767,704; 4,657,866; 4,927,762; or 4,560,655; WO 90/03430; WO 87/00195; U.S. Pat. Re. 30,985; or copending application Ser. Nos. 07/592,107 or 07/592,141, both filed on 3 Oct. 1990, may be used as culture media for the host cells. Any of these media may be supplemented as necessary with hormones and/or other growth factors (such as insulin, transferrin and/or epidermal growth factor), salts (such as sodium chloride, calcium, magnesium, and phosphate), buffers (such as HEPES) nucleosides (such as adenosine and thymidine), antibiotics (such as Gentamycin™), trace elements (inorganic compounds usually present at final concentrations in the micromolar range), and glucose or an equivalent energy source. Any other necessary supplements may also be included at appropriate concentrations that would be known to those skilled in the art. The culture conditions, such as temperature, pH and the like, are those previously used for the host cell selected for expression, and will be apparent to the ordinarily skilled artisan.

G. Glycosylation Variants

Glycosylation of polypeptides is typically either N-linked or O-linked. N-linked refers to the attachment of the carbohydrate moiety to the side-chain of an asparagine residue. The tripeptide sequences, asparagine-X-serine and asparagine-X-threonine, wherein X is any amino acid except proline, are recognition sequences for enzymatic attachment of the carbohydrate moiety to the asparagine side chain. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be involved in O-linked glycosylation.

The selectin ligands of the present invention are characterized by the prevalence of O-linked glycoslation sites. These may, for example, be modified by the addition of, or substitution by, one or more serine or threonine residue to the amino acid sequence of the ligand. For ease, changes are usually made at the DNA level, essentially using the techniques discussed hereinabove with respect to the amino acid sequence variants.

Chemical or enzymatic coupling of glycosydes to the ligands of the present invention may also be used to modify or increase the number or profile of carbohydrate substituents. These procedures are advantageous in that they do not require production of the polypeptide that is capable of O-linked (or N-linked) glycosylation. Depending on the coupling mode used, the sugar(s) may be attached to (a) arginine and histidine, (b) free carboxyl groups, (c) free hydroxyl groups such as those of cysteine, (d) free sulfhydryl groups such as those of serine, threonine, or hydroxyproline, (e) aromatic residues such as those of phenylalanine, tyrosine, or tryptophan or (f) the amide group of glutamine. These methods are described in WO 87/05330 (published 11 Sep. 1987), and in Aplin and Wriston, CRC Crit. Rev. Biochem., pp. 259–306 (1981).

Carbohydrate moieties present on a selectin ligand may also be removed chemically or enzymatically. Chemical deglycosylation requires exposure to trifluoromethanesulfonic acid or an equivalent compound. This treatment results in the cleavage of most or all sugars, except the linking sugar, while leaving the polypeptide intact. Chemical deglycosylation is described by Hakimuddin et al., Anal. Biochem. Biophys. 259, 52 (1987) and by Edge et al., Anal. Biochem. 118, 131 (1981). Carbohydrate moieties can be removed by a variety of endo- and exoglycosidases as described by Thotakura et al., Meth. Enzymol. 138, 350 (1987). Glycosylation is suppressed by tunicamycin as described by Duskin et al., J. Biol. Chem,. 257, 3105 (1982). Tunicamycin blocks the formation of protein-N-glycosydase linkages.

Glycosylation variants of the selectin ligands herein can also be produced by selecting appropriate host cells. Yeast, for example, introduce glycosylation which varies significantly from that of mammalian systems. Similarly, mammalian cells having a different species (e.g. hamster, murine, insect, porcine, bovine or ovine) or tissue (e.g. lung, liver, lymphoid, mesenchymal or epidermal) origin than the source of the selectin ligand, are routinely screened for the ability to introduce variant glycosylation as characterized for example, by elevated levels of mannose or variant ratios of mannose, fucose, sialic acid, and other sugars essential for selectin binding.

H. Covalent Modifications

Covalent modifications of a naturally occurring selectin ligand molecule or a sequence having a biological property in common with such molecule, are included within the scope herein. Such modifications are traditionally introduced by reacting targeted amino acid residues of the selectin ligand protein with an organic derivatizing agent that is capable of reacting with selected side-chains or terminal residues, or by harnessing mechanisms of post-translational modifications that function in selected recombinant host cells. The resultant covalent derivatives are useful in programs directed at identifying residues important for biological activity, for immunoassays of the selectin ligands, or for the preparation of anti-selectin ligand antibodies for immunoaffinity purification of the recombinant glycoprotein. For example, complete inactivation of the biological activity of the protein after reaction with ninhydrin would suggest that at least one arginyl or lysyl residue is critical for its activity, whereafter the individual residues which were modified under the conditions selected are identified by isolation of a peptide fragment containing the modified amino acid residue. Such modifications are within the ordinary skill in the art and are performed without undue experimentation.

Derivatization with bifunctional agents is useful for preparing intramolecular aggregates of the selectin ligand glycoprotein with polypeptides as well as for cross-linking the selectin ligand glycoprotein to a water insoluble support matrix or surface for use in assays or affinity purification. In addition, a study of interchain cross-links will provide direct information on conformational structure. Commonly used cross-linking agents include 1,1-bis(diazoacetyl)-2-phenylethane, glutaraldehyde, N-hydroxysuccinimide esters, homobifunctional imidoesters, and bifunctional maleimides. Derivatizing agents such as methyl-3-[(p-azidophenyl)dithio]propioimidate yield photoactivatable intermediates which are capable of forming cross-links in the presence of light. Alternatively, reactive water insoluble matrices such as cyanogen bromide activated carbohydrates and the systems reactive substrates described in U.S. Pat. Nos. 3,959,642; 3,969,287; 3,691,016; 4,195,128; 4,247,642; 4,229,537; 4,055,635; and 4,330,440 are employed for protein immobilization and cross-linking.

Certain post-translational modifications are the result of the action of recombinant host cells on the expressed polypeptide. Glutaminyl and aspariginyl residues are frequently post-translationally deamidated to the corresponding glutamyl and aspartyl residues. Alternatively, these residues are deamidated under mildly acidic conditions. Either form of these residues falls within the scope of this invention.

Other post-translational modifications include hydroxylation of proline and lysine, phosphorylation of hydroxyl groups of seryl or threonyl residues, methylation of the α-amino groups of lysine, arginine, and histidine side chains [T. E. Creighton, Proteins: Structure and Molecular Properties, W. H. Freeman & Co., San Francisco, pp. 79–86 (1983)].

Other derivatives comprise the novel peptides of this invention covalently bonded to a nonproteinaceous polymer. The nonproteinaceous polymer ordinarily is a hydrophilic synthetic polymer, i.e. a polymer not otherwise found in nature. However, polymers which exist in nature and are produced by recombinant or in vitro methods are useful, as are polymers which are isolated from nature. Hydrophilic polyvinyl polymers fall within the scope of this invention, e.g. polyvinylalcohol and polyvinylpyrrolidone. Particularly useful are polyvinylalkylene ethers such a polyethylene glycol, polypropylene glycol.

The selectin ligands may be linked to various nonproteinaceous polymers, such as polyethylene glycol, polypropylene glycol or polyoxyalkylenes, in the manner set forth in U.S. Pat. Nos. 4,640,835; 4,496,689; 4,301,144; 4,670,417; 4,791,192 or 4,179,337.

The selectin ligands may be entrapped in microcapsules prepared, for example, by coacervation techniques or by interfacial polymerization, in colloidal drug delivery systems (e.g. liposomes, albumin microspheres, microemulsions, nanoparticles and nanocapsules), or in macroemulsions. Such techniques are disclosed in Remington's Pharmaceutical Sciences, 16th Edition, Osol, A., Ed. (1980).

I. Selectin Ligand - Stable Plasma Protein Chimeras

A selectin ligand sequence can be linked to a stable plasma protein sequence as hereinbefore defined. The stable plasma protein sequence may, for example, be an immunoglobulin constant domain sequence. The resultant molecules are commonly referred to as selectin ligand-immunoglobulin chimeras.

In a preferred embodiment, the C-terminus of a sequence which contains the binding site(s) for a selectin, is fused to the N-terminus of the C-terminal portion of an antibody (in particular the Fc domain), containing the effector functions of an immunoglobulin, e.g. immunoglobulin $G_1$. It is possible to fuse the entire heavy chain constant region to the sequence containing the selectin binding site(s). However, more preferably, a sequence beginning in the hinge region just upstream of the papain cleavage site (which defines IgG Fc chemically; residue 216, taking the first residue of heavy chain constant region to be 114 [Kobet et al., Supra], or analogous sites of other immunoglobulins) is used in the fusion. In a particularly preferred embodiment, the amino acid sequence containing the selectin binding site(s) is fused to the hinge region and $C_H2$ and $C_H3$ or $C_H1$, hinge, $C_H2$ and $C_H3$ domains of an $IgG_1$, $IgG_2$ or $IgG_3$ heavy chain. The precise site at which the fusion is made is not critical, and the optimal site can be determined by routine experimentation.

J. Purification Of The Selectin Ligands

The selectin ligand may be recovered and purified from recombinant cell cultures by known methods, including ammonium sulfate or ethanol precipitation, acid extraction, anion or cation exchange chromatography, hydroxyapatite chromatography, immunoaffinity chromatography and lectin chromatography. Other known purification methods within the scope of this invention utilize reverse-phase HPLC chromatography using anti-selectin ligand antibodies are useful for the purification of the ligands of the present invention.

A particularly advantageous purification scheme, specifically developed for the purification of the L-selectin ligand, will be described in Example 1. This method takes advantage of a unique selectin receptor-immunoglobulin chimera (referred to as L-selectin-IgG), produced by recombinant methods, which is able to precipitate the corresponding (sulfate-labeled) ligand.

K. Therapeutic Compositions

The selectin ligands of the present invention can be used to block the binding of a corresponding selectin receptor to its native ligand. For example, the L-selectin ligand effectively blocks the binding of an L-selectin receptor on a circulating leukocyte to its native ligand on an endothelial cell. This property is useful for treating a symptom or condition associated with excessive binding of circulating leukocytes to endothelial cells, such as inflammation associated with rheumatoid arthritis, psoriasis, multiple sclerosis, etc.

The selectin ligands of the present invention can be formulated according to known methods to prepare pharmaceutically useful compositions, whereby the ligand is combined in admixture with a pharmaceutically acceptable carrier. Suitable carriers and their formulations are described in Remington's Pharmaceutical Sciences, 16th ed., 1980, Mack Publishing Co., edited by Oslo et al., specifically incorporated by reference. These compositions will typically contain an effective amount of the ligand, for example, from on the order of about 0.5 to about 10 mg/ml, together with a suitable amount of carrier to prepare pharmaceutically acceptable compositions suitable for effective administration to the patient. The ligands may be administered parenterally or by other methods that ensure its delivery to the bloodstream in an effective form.

Compositions particularly well suited for the clinical administration of the ligands used to practice this invention include sterile aqueous solutions or sterile hydratable powders such as lyophilized protein. Typically, an appropriate amount of a pharmaceutically acceptable salt is also used in the formulation to render the formulation isotonic.

Dosages and desired drug concentrations of pharmaceutical compositions of this invention may vary depending on the particular use envisioned.

K. Monoclonal Antibodies

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, the monoclonal antibodies of the invention may be made using the hybridoma method first described by Kohler & Milsrein, Nature 256:495 (1975), or may be made by recombinant DNA methods [Cabilly, et al., U.S. Pat. No. 4,816,567].

In the hybridoma method, a mouse or other appropriate host animal, such as hamster is immunized with the selectin ligand protein by subcutaneous, intraperitoneal, or intramuscular routes to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell [Goding, Monoclonal Antibodies: Principles and Practice, pp.59–103 (Academic Press, 1986)].

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high level expression of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA. Human myeloma and mouse-human heteromyeloma cell lines also have been described for the production of human monoclonal antibodies [Kozbor, J. Immunol. 133:3001 (1984); Brodeur, et al., Monoclonal Antibody Production Techniques and Applications, pp.51–63 (Marcel Dekker, Inc., New York, 1987)].

Culture medium in which hybridoma cells are growing is assayed for production of monoclonal antibodies directed against TNFR1. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The affinity of the monoclonal antibody for binding the corresponding ligand can, for example, be determined by the Scatchard analysis of Munson & Pollard, Anal. Biochem. 107:220 (1980).

After hybridoma cells are identified that produce antibodies of the desired specificity, affinity, and/or activity, the clones may be subcloned by limiting dilution procedures and grown by standard methods. Goding, Monoclonal Antibodies: Principles and Practice, pp.59–104 (Academic Press, 1986). Suitable culture media for this purpose include, for example, Dulbecco's Modified Eagle's Medium or RPMI-1640 medium. In addition, the hybridoma cells may be grown invivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, Morrison, et al., Proc. Nat. Acad. Sci. 81:6851 (1984), or by covalently joining to the immunoglobulin coding sequence all or part of the coding sequence for a non-immunoglobulin polypeptide. In that manner, "chimeric" or "hybrid" antibodies are prepared that have the binding specificity of an anti-selectin ligand monoclonal antibody herein.

Typically such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for a selectin ligand and another antigen-combining site having specificity for a different antigen.

Chimetic or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

For diagnostic applications, the antibodies of the invention typically will be labeled with a detectable moiety. The detectable moiety can be any one which is capable of producing, either directly or indirectly, a detectable signal. For example, the detectable moiety may be a radioisotope, such as $^{3}H$, $^{14}C$ $^{32}P$, $^{35}S$, or $^{125}I$, a fluorescent or chemiluminescent compound, such as fluorescein isothiocyanate, rhodamine, or luciferin; radioactive isotopic labels, such as, e.g., $^{125}I$, $^{32}P$, $_{14}C$, or $^{3}H$, or an enzyme, such as alkaline phosphatase, beta-galactosidase or horseradish peroxidase.

Any method known in the art for separately conjugating the antibody to the detectable moiety may be employed, including those methods described by Hunter, et al., Nature 144:945 (1962); David, et al., Biochemistry 13:1014 (1974); Pain, et al., J. Immunol. Meth. 40:219 (1981); and Nygren, J. Histochem. and Cytochem. 30:407 (1982).

The antibodies of the present invention may be employed in any known assay method, such as competitive binding assays, direct and indirect sandwich assays, and immunoprecipitation assays. Zola, Monoclonal Antibodies: A Manual of Techniques, pp.147–158 (CRC Press, Inc., 1987).

Competitive binding assays rely on the ability of a labeled standard (which may be a selectin ligand or an immunologically reactive portion thereof) to compete with the test sample analyte (selectin ligand) for binding with a limited amount of antibody. The amount of selectin ligand in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three part complex. David & Greene, U.S. Pat No. 4,376, 110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

The invention will further be illustrated by the following non-limiting examples.

III. EXAMPLES

EXAMPLE 1

Identification of Surface Glycoproteins on Endothelial Cells Recognized by L-selectin This example shows that recombinant L-selectin selectively binds $^{35}SO_4$-labeled macromolecules from lymph nodes. In particular, two sulfated, fucosylated and sialylated glycoproteins have been identified.

A. Metabolic Labeling of Organs with $^{35}S$-sulfate

Mesenteric or peripheral (cervical, brachial, axillary) lymph nodes were collected from 8–16 week old female ICR mice. The lymph nodes were cut into 1 mm thick slices with a razor blade and the slices (typically, 0.2 g of wet weight) were suspended in 1 ml of RPMI-1640 containing 25 mM HEPES, 100 U/ml Penicillin G, 100 µg/ml streptomycin, and 200 µCi carrier-free [$^{33}S$] sodium sulfate (ICN Biochemicals Inc., Costa Mesa, Calif.) according to the procedure of Ager, J. Cell Sci., 87:133 (1987). After incubation of 37° C. for 4 hr, the slices were washed extensively in Dulbecco's phosphate-bufferred saline (PBS), and then homogenized in 1 ml of lysis buffer (2% Triton X-100 in PBS containing 1 mM PMSF, 1% (v/v) aprotinin, 10 µg/ml pepstatin, 0.02% $NaN_3$) with a Potter-Elvehjem homogenizer on ice. Lysis was continued for 1 hr on a rocker at 4° C. The lysate was centrifuged at 10,000×g for 1 hr at 4° C. EDTA was added to the supernatant at a final concentration of 2 mM and the supernatant was precleared by rocking with Affi-Gel Protein A (250 µl of packed beads, BioRad Laboratories, Richmond, Calif.) overnight at 4° C.

B. Identification of the components Adsorbed to L-selectin-IgG Beads

Affi-Gel Protein A (10 µl packed beads) was incubated with 30 µg of either L-selectin-IgG (WO 91/08298 published 13 Jun. 1991), CD4-IgG (prepared according to Capon et al., Nature 337:525 (1989) or human $IgG_1$ (Calbiochem, La Jolla, Calif.) in 1 ml of PBS rocking overnight at 4° C. The beads (referred to as L-selectin-IgG beads, CD4-IgG beads and huIgG-beads) were washed 3X in PBS and once with lysis buffer. The CD4-IgG and huIgG beads were used as controls.

The precleared lysate described in Section A, above, was centrifuged at 10,000×g for 10 sec, $CaCl_2$ was added to the supernatant at a final concentration of 5 mM, and the supernatant was mixed immediately with either L-selectin-IgG beads, CD4-IgG beads or huIgG-beads (typically 200 µl of precleared lysate per 10 µl packed beads), and incubated for 4 hr at 4° C. on a rocker. The beads were washed 6X with lysis buffer, transferred to a new tube, and washed once more with lysis buffer.

The materials bound to the L-selectin-IgG beads were solubilized by boiling in SDS in the presence of 2-mercaptoethanol, electrophoresed on SDS-polyacrylamide gels (9 or 10%) and subjected to fluorography with ENTENSIFY or EN³HANCE (NEN). By fluorography, the 50 kD component tended to be more diffuse with ENTENSIFY than EN³HANCE. In the reprecipitation experiment, the SDS-solubilized sample was electrophoresed on a 7.5% SDS-gel with prestained standards (BioRad, high range) as markers. The region around 50 kD on the gel was excised by utilizing prestained ovalbumin (49.5 kD) as a position marker, and the protein electroeluted (BioRad model 422) into Laemmli running buffer at 60 mA overnight. The eluate was concentrated and the buffer was exchanged into 10 mM CAHPS in PBS on a Centricon 30 unit (Amicon, Danvers, Mass.), followed by incubation with L-selectin-IgG beads CD4-IgG or huIgG beads as described above. For the analysis of crude lysate, 200 µl of the precleared lysate was precipitated with cold acetone (80% v/v) and then subjected to electrophoresis as above.

L-selectin-IgG beads precipitated a diffuse 50 kD component (apparent molecular weight range is 50 kD–58 kD) from [$^{35}$S]-sulfate-labeled mesenteric lymph nodes (MLN) or peripheral lymph nodes (PN). A band of ≈90 kD (83 kD–102 kD), relatively minor in terms of sulfate incorporation, was also observed in most analyses. In control precipitations, CD4-IgG and huIgG beads did not recognize the 50 kD major component or the 90 kD component in the lysates. When crude lysates were directly analyzed, the 50 kD component represented the major constituent among several other bands. The tissue distribution of the 50 kD component was further examined by applying the identical protocol for [$^{35}$S] sulfate-labeling and precipitation with LHR IgG to a number of organs. Among lymphoid tissues, only peripheral lymph nodes and mesenteric lymph nodes showed the 50 kD and 90 kD bands, while Peyer's patches, spleen, and thymus were negative for both. Non-lymphoid organs such as kidney, liver, cerebrum, and cerebellum were also completely negative.

L-selectin-IgG beads precipitated the 50 kD component when calcium was present, but not in its absence. The specificity of the interaction was further examined with the use of MEL-14 mAb. Preincubation of L-selectin-IgG beads with this antibody completely blocked the binding of the 50 kD band to the beads, whereas a class-matched control antibody (anti-CD45) had no effect. Fucoidin completely blocked the precipitation of the 50 kD component by L-selectin-IgG beads, while control polysaccharides (chondroitin sulfate B, chondroitin sulfate A, keratan sulfate) were completely inactive. Further, the presence of PPME significantly reduced the intensity of the 50 kD band, although a relatively high concentration was required. A control yeast mannan (mnn 2) had no effect at the same concentration. The precipitation of the minor 90 kD band by L-selectin-IgG beads was also calcium dependent, inhibitable by MEL-14 mAb, and blocked by fucoidin and PPME.

Finally, sialidase treatment of the glycoproteins was found to inhibit binding by L-selectin-IgG. Thus, sialic acid on the glycoproteins is apparently essential for binding. This result is in agreement with previous characterizations of interactions between selectins and their ligands.

EXAMPLE 2

Purification of the 50 kD L-selectin ligand for cloning and sequence determination The work described in Example 1 demonstrated that the L-selectin-IgG chimera could be utilized to biochemically characterize the ~50 kD sulfated endothelial ligand produced by peripheral and mesenteric lymph nodes. Further work has demonstrated that this ligand is readily shed into the medium when peripheral lymph nodes (PLN) are placed into organ culture (S. Watson-unpublished observations). Thus, the initial step in the purification of the L-selectin ligand for sequence determination was to produce large quantities of medium conditioned by murine PLN. A second observation that allowed for a dramatic purification was that ~50 kD sulfated L-selectin ligand was soluble after treatment of conditioned medium with chloroform-methanol. This step resulted in a >350 fold purification of the sulfated ligand. The next purification step consisted of a wheat germ agglutinin affinity column, which took advantage of the apparently high content of carbohydrate in this ligand. The final purification step utilized an L-selectin-IgG chimera affinity column to purify the ligand. This final step assured that the material contained within the ~50 kD region would correspond to a glycoprotein that could bind with relatively high affinity to L-Selectin.

Mesenteric or peripheral (cervical, brachial, and axillary) lymph nodes were collected from 8–16-wk-old female ICR mice. Mice were killed and their mesenteric lymph nodes were removed. Typically, a single batch of conditioned medium was made from the mesenteric nodes of 30 mice. Occasionally, a small number (approximately 5% of the total lymph node weight) of peripheral lymph nodes were also added. The nodes were cut into approximately 1-mm-thick slices with a razor blade and the slices were added to the standard cell culture medium RPMI-1640 supplemented with 25 mM HEPES buffer, i U/ml penicillin and 1 µg/ml streptomycin in a 100-ml cell culture bottle. The ratio of medium to nodes was 6 ml/30 mesenteric lymph nodes.

The culture bottle was placed in a 37° C. incubator. After 4 hours, the medium was poured into a 15-ml conical tube and centrifuged at 500×g for 10 minutes to remove large tissue debris. The supernatant was centrifuged again in a 15-ml Corex tube at 20,000×g for 15 minutes. The resultant supernatant was first poured through Nitex screen to remove fatty particles that do not pellet during centrifugation, and was then snap-frozen with liquid nitrogen and stored at −20° C.

For the purpose of monitoring the protein purification scheme, $^{35}$SO$_4$-labeled Sgp50 was added to the conditioned medium prepared as hereinabove described. This material was prepared by labeling 5 mice mesenteric lymph nodes in 1 ml of the above-described culture medium with 0.5 mCi Na$^{35}$SO$_4$ (ICN). After 4 hours, the conditioned cell culture medium was removed and centrifuged in a microfuge for 10 minutes. The supernatant was removed and precleared by adding to 100 µl packed protein A-agarose beads (Zymed Corp.), and rocking overnight at 4° C. The precleared medium was added to a 3 ml covalently crosslinked LEC-IgG-protein A-agarose (LEC x protein A-agarose) column prepared with 10 mg L-selectin-IgG per i ml packed protein A-agarose (Zymed) following the procedure outlined on pages 522–523 of Antibodies. A Laboratory Manual (1988) Harlow and Lane, Cold Spring Harbor Laboratory. After rocking for 6 hours to overnight with L-selectin x protein A-agarose, the column was washed with 10 volumes Dulbecco's phosphate-buffered saline (PBS) and the purified material (50 kD L-selectin ligand, a.k.a. GlyCAM) was eluted with 10 ml 4 mM EDTA in PBS. This material was concentrated on a Centricon 30 (Amicon Corp.) to a final volume of approximately 100 µl. About 60,000 cpm of material were obtained.

To produce purified protein for microsequencing analysis, four batches (approximately 120 mice) of conditioned medium (24 ml) were thawed. 50 µl of $^{35}$SO$_4$-labeled Sgp50 (32,000 cpm) was added. Nine volumes (216 ml) of chloroform:methanol (2:1) was added and rocked in 50-ml conical tubes for 30 minutes at room temperature and centrifuged at 500×g for 20 minutes. The upper aqueous layer was collected and the "interface" layer was recentrifuged to extract as much aqueous layer as possible. The chloroform:methanol extraction was repeated. In order to see an aqueous layer, approximately 20 ml of PBS was added. The aqueous layer was collected and residual chloroform:methanol evaporated by stirring the aqueous layer for 3 hours in a one-liter beaker in a warm water bath in the fume hood. The material, now called <C:M ("after chloroform:methanol partitioning"), was then dialyzed against PBS for 4 hours. In a similar preparation, 1 385-fold purification was achieved. The dialyzed <C:M, with 19200 cpm, was rocked overnight at 4° C. with 4 ml wheat germ agglutinin (WGA)-agarose gel (Vector Laboratories). The gel was collected in a column, washed with 40 ml PBS and eluted with 0.2 M n-acetylglucosamine in PBS. In a similar experiment, an additional 4.4-fold purification was achieved. This material, containing approximately 15000 cpm representing the equivalent of 60 mice, was concentrated on a Centricon 30, and run on a 10% SDS-gel under standard Laemmli procedures. In a similar experiment, a final purification on LEC x protein A-agarose yielded an overall 60606-fold purification. The protein was then electroblotted in a BioRad miniblotter (250 mA, constant current for 2 hours) onto ProBlott membrane (Applied Biosystems Incorp.). The membrane (blot) was stained and destained with Coomassie R-250 following the manufacturer's recommendation. The blot was air-dried and autoradiography performed with Kodak XAR film.

The purified material was then subjected to gas-phase microsequencing.

EXAMPLE 3

Protein Sequence Determination

The polypeptide sequence was determined by gas-phase microsequencing of the material purified as described in Example 2. The protein eluted from the L-Selectin-IgG affinity column was run on a 10% SDS-gel, electroblotted onto a Problott membrane (Applied Biosystems Inc.), stained with Coomassie R-250 and destained. The blot was air-dried and exposed to Kodak XAR film to detect the position of the sulfate labelled ligand. This region of the gel was cut out and subjected to gas-phase microsequencing. Sequencing was essentially performed as hereinbefore described.

Figures 3A, 3B:
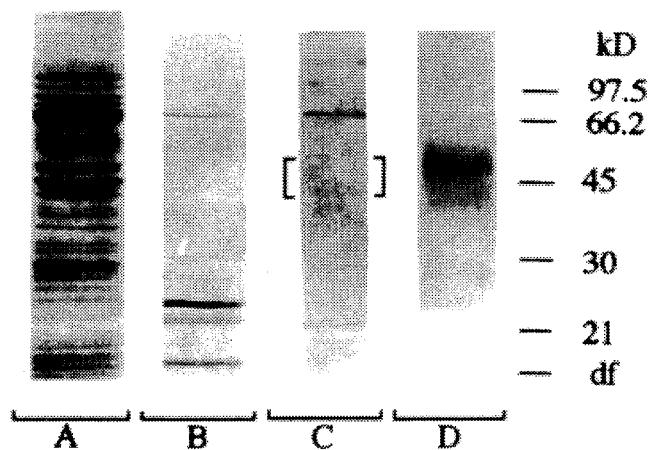
FIG. 3A. Illustrates the purification and N-terminal amino acid sequence of the ~50 kD L-selectin ligand. The purification of ligand from conditioned medium was monitored by following added $^{35}$S-labeled ligand. Lane A, Starting conditioned medium. Lane B, Aqueous layer after chloroform:methanol partitioning. Lane C, LEC-IgG bound material, the bracketed area was cut out for gas-phase protein sequencing. Lanes A–C are ProBlott membrane stained with Coomassie R-250. Lane D is the autoradiograph of Lane C.
FIG. 3B. N-terminal amino acid sequence (SEQ. ID. No.: 1)

Polypeptide sequencing revealed an unambiguous stretch of 25 amino acids at approximately the 5 pM level (FIG. 3B (SEQ. ID. No.:1)).

EXAMPLE 4 cDNA Cloning and Sequence Analysis of the ~50 kD L-Selectin Ligand

A murine peripheral lymph node cDNA library was constructed using an InvitroGen cDNA library kit and poly A+ RNA isolated from murine peripheral lymph nodes. A redundant oligonucleotide probe pool was derived from residues 9–17 of the N-terminal sequence (QMKTQPMDA) (SEQ. ID. No.: 3) using degenerate codons selected on the basis of the mammalian codon usage rule. Codons were CAG, ATG, AAG, AAA, ACA, ACT, ACC, CCA, CCT, CCC, GAT, or GAC. Only GC was used for the 5' Ala codon. The 26-mer oligonucleotide was $^{32}$P labeled by polynucleotide kinase and hybridized to duplicate nitrocellulose filters derived from 20 plates containing 1 million gT10 bacteriophage in 20% formamide, 5X SSC (150 mM CaCl, 15 mM trisodium citrate), 50 mM sodium phosphate (pH7.6), 5X Denhardt's solution, 10% dextran sulfate and 20 micrograms per ml denatured, sheared salmon sperm DNA at 42° C. overnight. The filters were washed in 1X SSC, 0.1% SDS at 42° C. twice for 30 minutes and autoradiographed at −70° C. overnight. A single duplicate positive phage was plaque purified, and the Eco R1 insert was subcloned into the pGEM vector. The entire nucleotide sequence of both strands was obtained by supercoin sequencing with the Sequenase kit. For in situ hybridization and Northern blot analysis, a polymerase chain reaction fragment lacking the poly A tail was synthesized then subcloned into the pGEM vector (PROMEGA). The nucleotide sequence of the encoded cDNA is shown in FIG. 4. The clone contained a short (about 600 bp) cDNA with a single open reading frame of 151 amino acids. A "Kozak box" (CCACCATGA) was found surrounding the first encoded methionine [Kozak, M. Cell Biology 115:887 (1991)]. This methionine was followed by a 19 amino acids long, highly hydrophobic sequence that appears to function as a signal sequence for translocation of the protein into the secretory pathway. This region is followed by a sequence corresponding almost exactly to that determined by N-terminal sequencing of the L-selectin-IgG bound material. The signal sequence-processed 132 amino acid protein is extremely rich in serine and threonine, with about 29% of the encoded amino acids corresponding to these residues.

Figure 3C:
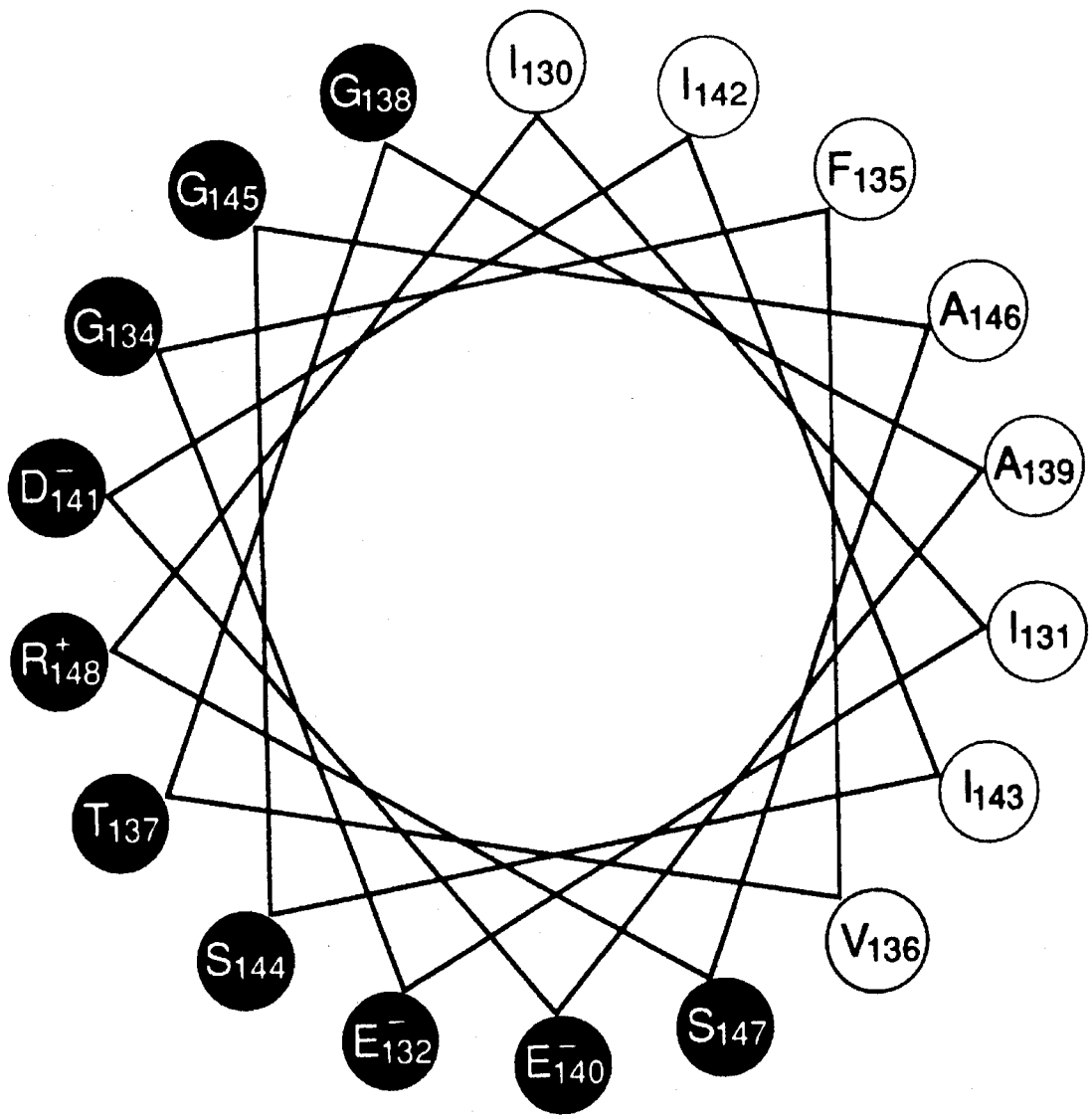
FIG. 3C. The C-terminal 21 amino acids were analyzed by the wheel program. This program displays a view down the barrel of a helical region and illustrates the amino acid residues surrounding the helix. Apolar amino acids are shown in open boxes and polar amino acids are shown in shaded boxes.
Figure 3D:
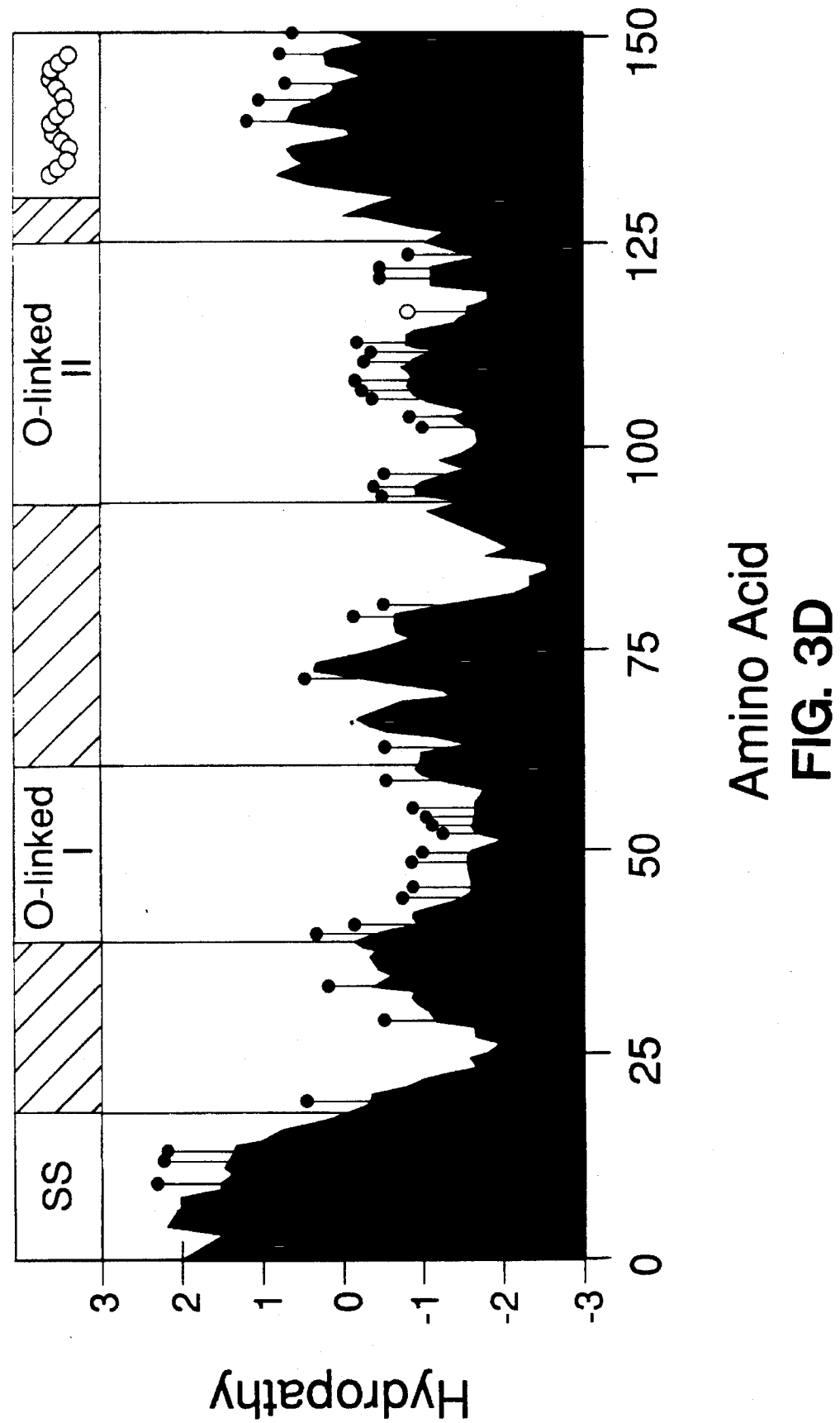
FIG. 3D. Illustrates a hydropathy plot derived from the predicted amino acid sequence in A. The dark balls correspond to serine or threonine residues, while the open ball is the ASN of the single potential N-linked glycosylation site. The predicted domain structure of the ~50 kD ligand is shown above, with the signal sequence (SS), O-linked regions I and II and the C-terminal amphipathic helical region.

Perhaps more interestingly, these serine and threonine residues were found to be clustered in two regions of the glycoprotein (FIG. 3D). Region I (residues 42–63) was found to contain 12 serine or threonine residues (~55%) while region II (residues 93–122) was found to contain 14 serine or threonine residues (~48%). Within these regions, serine and threonine residues were usually found clustered in groups of two, three or four. The protein lacked cystsine residues, and there was one potential N-linked glycosylation site (residues 115–117). The lack of cystsine residues was consistent with previous data which demonstrated that the mobility of the sulfate-labeled ligand on SDS-polyacrylamide gels was not affected by the absence of disulfide reducing agents [S. Imai and S. Rosen unpublished observations]. In addition, the single potential N-linked site agreed with the previously demonstrated paucity of N-glycanase-sensitive carbohydrate side-chains on the ~50 kD ligand. Finally, the molecular weight of the processed protein was found to be ~14,154 kD. Since the molecular weight of the isolated L-selectin ligand is ~50 kD, this result suggests that ~70 kD of the glycoprotein mass is O-linked carbohydrate [Carraway and Hull, BioAssays 10(4), 117–121 (1989)], a result that is consistent with the inability to stain the isolated glycoprotein with Coomassie blue.

Examination of the C-terminus of the protein encoded by this cDNA revealed a mildly hydrophobic domain, but no obvious transmembrane anchoring motif. While it is possible that this region corresponds to a signal directing the addition of a phosphatidyl inositol (PI) tail, treatment of lymph node sections with phosphatidyl inositol phospholipase C (PIPLC) does not appear to remove the ligand from the endothelium (M. Singer, S. Watson, R. Mebius-unpublished observations). While this result does not disprove the possibility that the ~50 kD ligand associates with the cell surface using a PI tail, it suggests that other possible linkages to the cell surface may be utilized by this glycoprotein. Examination of the C-terminal 21 amino acids by a program that searches for amphipathic helices reveals that the C-terminus of this glycoprotein encodes a highly significant amphipathic helix (FIG. 3C), with one face of this potentially helical region containing apolar residues while the other face contains polar residues [J. Mol. Biol. 81:155 (1984)].

EXAMPLE 5

Production of Antibodies Against Peptides

In order to ultimately prove that the isolated cDNA encodes a sequence corresponding to the protein backbone of an L-selectin ligand, we produced peptides derived from the amino acid sequence predicted from the nucleotide sequence of the isolated ligand cDNA were produced on an Applied Biosystems peptide synthesizer. Peptides from the N-terminus (CAM01:LPSKDELQMKTC), the middle region of the protein (CAM02:CKEPSIFREELISKD), and the C-terminus of the protein (CAM05:CIISGASRITKS) (SEQ. IDs.: 4, 5 and 6) were coupled to keyhole limpet hemocyanin through the added, underlined cysteine residues and injected into rabbits following a standard immunization protocol. Preimmune sera and sera from vaccinated, boosted rabbits were collected (the rabbit polyclonal antipeptide sera are now designated CAM01, CAM02, CAM05), and each sera was tested for its ability to immunoprecipitate sulfate labeled L-selectin ligand that was purified by binding to the L-selectin-IgG chimera as described above.

Figure 5A:
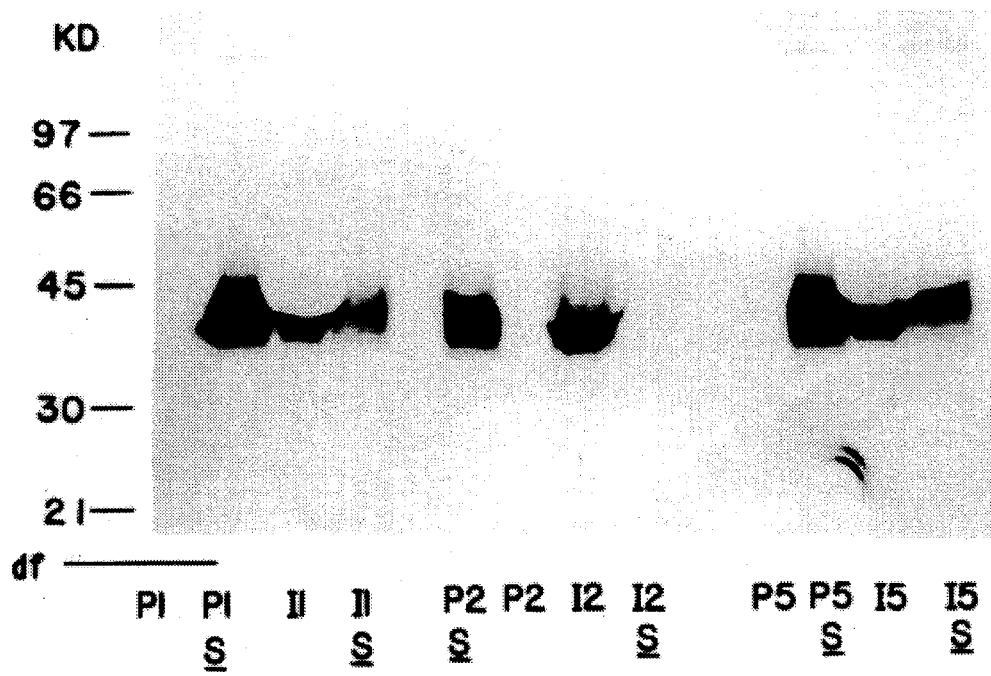
FIGS. 5A and 5B show the immunoprecipitation of the L-selectin purified ~50 kD ligand by peptide antibodies. In these figures
PI=Preimmune CAM01 - beads;
PI/S=Preimmune CAM01 - supernatant left after immunoprecipitation;
I1=Immune CAM01 - beads;
I1/S=Immune CAM1 - supernatant left after immunoprecipitation.
Figure 5B:
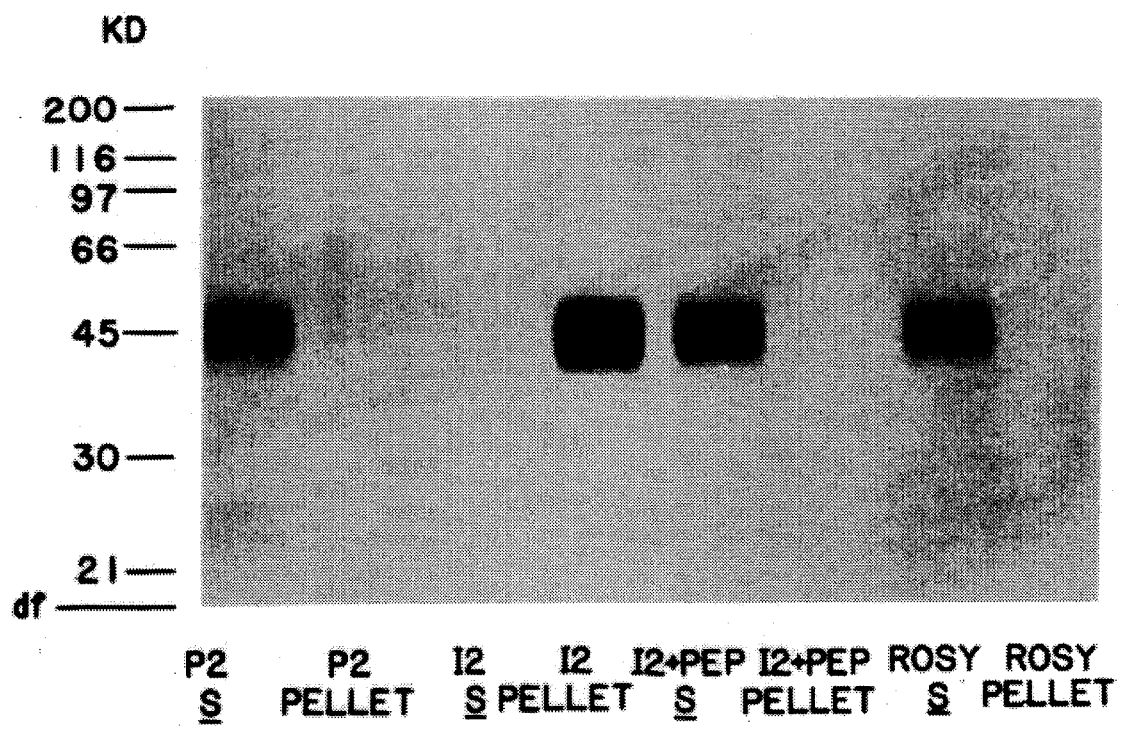

To verify that the cloned protein is the same as the $^{35}$S-labeled material purified from conditioned medium with the L-selectin IgG chimera, immunoprecipitation of L-selectin-IgG purified $^{35}$S-labeled material was performed. The following procedure was used for two separate experiments. For the preparation of immunoprecipitation beads, 25 µl packed protein A-Sepharose beads (Zymed Laboratories) +25 µl rabbit serum+350 µl PBS are rocked together in a microfuge tube for 3 hours, 4° C. Each tube is washed 3 times with PBS to remove unbound immunoglobulin and only the 25 µl beads remains. 60 µl of PBS containing approximately 6,000 cpm of L-selectin-IgG purified $^{35}$S-labeled material is added. This is incubated on ice for 3 hours, flicking the tube every 15 minutes. After 3 hours, the microfuge tube is spun to pellet the beads. 45 µl of supernatant is taken off and mixed with 15 µl 4X Laemmli sample buffer and boiled for SDS-PAGE analysis. The pelleted beads are washed 3 times with PBS, transferred to a new tube, and supernatant decanted to leave 45 µl final volume in tube. 15 µl 4X Laemmli sample buffer is added and the tubes are boiled for SDS-PAGE analysis. This SDS-gel run was under reducing conditions. Immunoglobulin heavy chain runs at 50 kD under reducing conditions and the labeled band is compressed. In this experiment, none of the preimmune sera interact with the label, whereas, CAM01 and CAM05 have partial effects and CAM02 totally immunoprecipitates the band. This experiment was repeated with CAM02 with the following differences. The gel was run under non-reducing conditions so that the 50 kD band would not be compressed. (We have previously established that the L-selectin-IgG purified $^{35}$S-labeled material does not change mobility in an SDS-gel under reducing conditions.) Also, for one tube, the CAM02 antibody coated-beads were preincubated with 1 mg/ml CAM02 peptide for 30 minutes on ice in order to show specificity of the antibody-antigen interaction. Finally, an irrelevant control peptide antibody against the C-terminus peptide of L-selectin (called ROSY 1B), also prepared by Caltag using similar protocols, was tested. Both gels were subjected to fluorography with Enhance (New England Nuclear) and autoradiography with Kodak Xar film. CAM02 completely immunoprecipitates the L-selectin-IgG purified $^{35}$S-labeled material, CAM02 preimmune and ROSY 1B have no effect. The free CAM02 peptide blocks the specific immunoprecipitation. The results are shown in FIGS. 5A and B.

EXAMPLE 6

Expression of the L-Selectin Ligand

FIG. 6 shows a Northern blot analysis of the mRNA encoding the ~50 kD L-selectin ligand. As can be seen in FIG. 6A, the mRNA is encoded in the poly A+ fraction and corresponds to a discrete band of ~0.7 kD. The sharpness of the band argues against a significant level of alternative RNA splicing, and rescreening of the murine PLN cDNA library with the isolated ligand clone has not revealed any other spliced forms of the message. Induction of an inflammatory response in the region drained by a lymph node shows a relative decrease in the amount of mRNA encoding the ligand, presumably due to the large contribution of poly A+ mRNA from newly migrating lymphocytes. This result suggests that the ligand does not appear to be dramatically induced in the PLN HEV during inflammation, although it is difficult to make quantitative conclusions from this experiment. Inspection of the expression of this mRNA in different regional lymph nodes demonstrates that it is expressed in all regional PLN that we have examined (FIG. 6B).

Figure 6A:
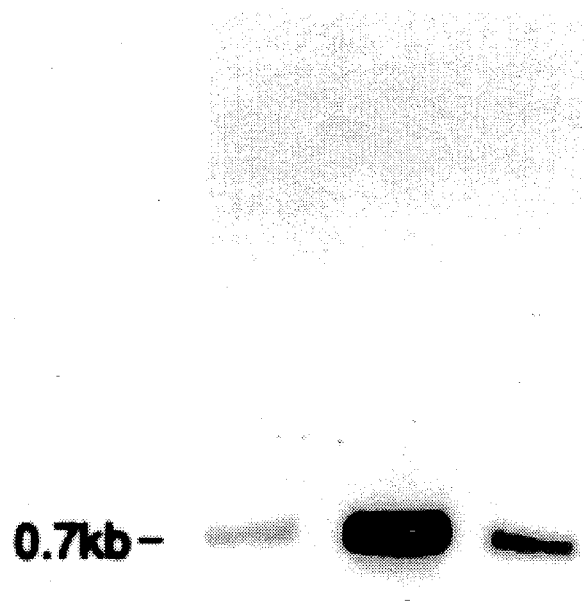
FIG. 6. Northern blot analysis of the expression of the mRNA encoding the ~50 kD L-selectin ligand. A. Total(a) or poly A+ (b, c) RNA was isolated from normal (a,b) or inflamed (c) peripheral lymph nodes, run on formaldehyde gels and analyzed by Northern blot analysis with the cDNA shown in FIG. 4. B. Poly A+ RNA was isolated from a) brachial, b) axillary, c) cervical, d) popliteal, and e) total peripheral lymph node and hybridized on Northern blots with the ligand cDNA as described in A., C. and D. Poly A+ RNA was isolated from a) peripheral lymph nodes, b) liver, c) Peyer's patch, d) thymus, e) skeletal muscle, f) mesenteric lymph nodes, g) testes, h) lung, i) heart, j) spleen, k) brain, and l) kidney and hybridized on Northern blots with C. the cDNA corresponding to the L-selectin ligand or D. a chicken beta actin cDNA.
Figure 6B:
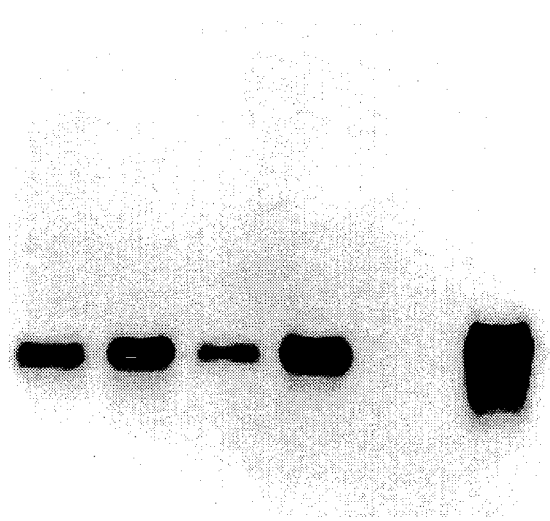
Figure 6C:
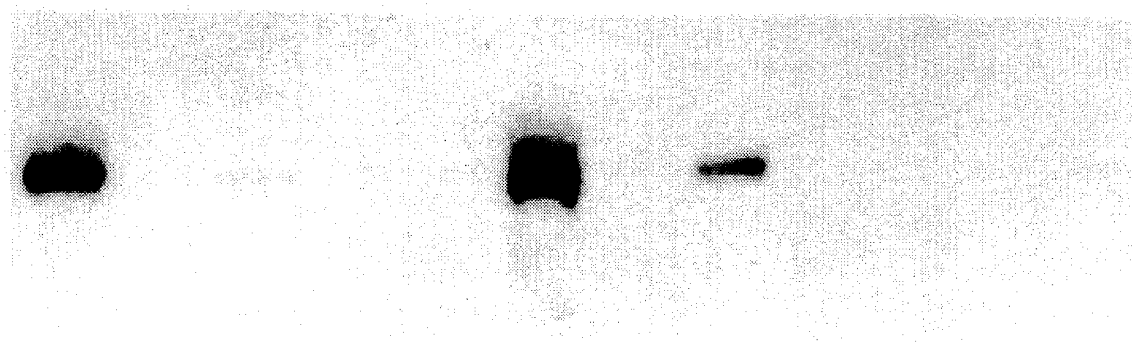
Figure 6D:

Analysis of the expression of the mRNA encoding the L-selectin ligand in a number of different lymphoid and non-lymphoid tissues reveals that this sequence is expressed in a highly tissue-specific manner. FIG. 6C shows that the mRNA corresponding to the ligand is expressed strongly in both mesenteric and peripheral lymph nodes. This agrees with previous work which demonstrated that the sulfate-labeled ligand was found to be expressed only in these two organs. The message is also expressed at significant levels in the lung and at very low levels in the Peyer's patches. The mRNA is not detectable in a number of non-lymphoid organs nor is it found in two other lymphoid organs: spleen and thymus. This latter result strongly suggests that the ligand may be significantly expressed in only a subset of the vasculature: i.e. the HEV found in peripheral lymphoid tissues.

In order to prove that the ligand mRNA is expressed in the HEV, in situ hybridization was performed. Tissues were analyzed for ligand expression by in situ hybridization using previously described methods (Wilcox et al., Proc. Natl. Acad, Sci. USA 86: 2839 (1989)). Peripheral lymph nodes and sections of small intestine having a Peyer's patch were harvested from mice, fixed in paraformaldehyde followed by sucrose immersion. Tissues were embedded in OCT compound (Miles Scientific), frozen in isopentane and sectioned in 8 micron sections. The sections were thaw-mounted on Vectabond-coated slides (Vector Laboratories). $^{35}$S-labeled RNA probes were generated in the sense and anti-sense orientations using previously described methods (Melton et al. 1984). For hybridization, sections were treated sequentially with 4% paraformaldehyde (10 min.), proteinase K (1 microgram/ml, 10 min.) followed by prehybridization with 100 microliters of hybridization buffer (50% formamide, 0.03 M NaCl, 20 mM Tris-HCl, 5 mM EDTA, 1X Denhardt's solution, 5% Dextran Sulfate, 10 mM dithiothreitol) at 42° C. for 2 Hrs. Probes were added at a final concentration of 8×10$^6$ cpm/ml and then incubated overnight at 55° C. Slides were washed with 2X SSC containing 10 mM beta mercaptoethanol (BME), 1 mM EDTA followed by a 30 minute treatment (20 micrograms/ml for 30 minutes). A high stringency wash consisting of 0.1X SSC containing EDTA and BME was done at 55° C. for 2 hrs. Slides were washed in 0.5 X SSC, dehydrated in increasing concentrations of ethanol and vacuum dessicated. Slides were dipped in NTB2 nuclear emulsion (Kodak) and exposed for up to 5 weeks.

Figure 7A:
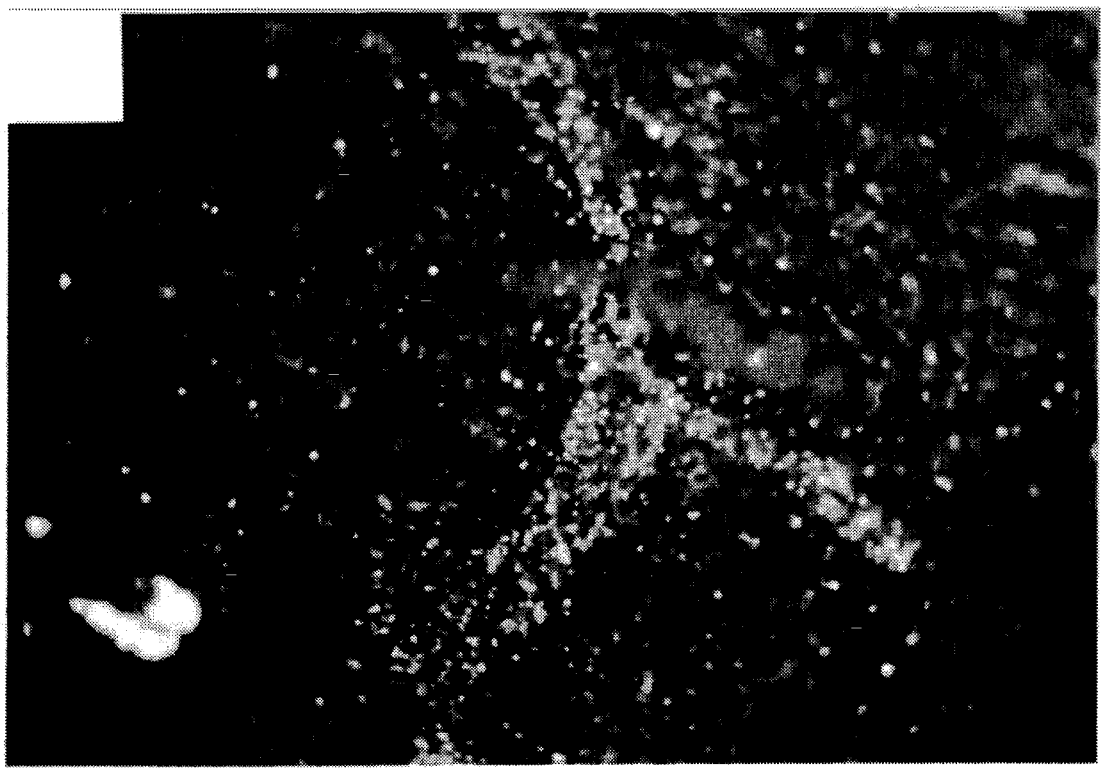
FIG. 7. (Parts A and B) In Situ hybridization analysis of the expression of the mRNA encoding the ~50 kD L-selectin ligand. Peripheral lymph node sections were hybridized with either an anti-sense (A) or sense (B) hybridization probe corresponding to the L-selectin ligand cDNA, washed, exposed to emulsion for 6 weeks and developed. The morphology of the HEV is shown with a dotted line surrounding the venule.
Figure 7B:
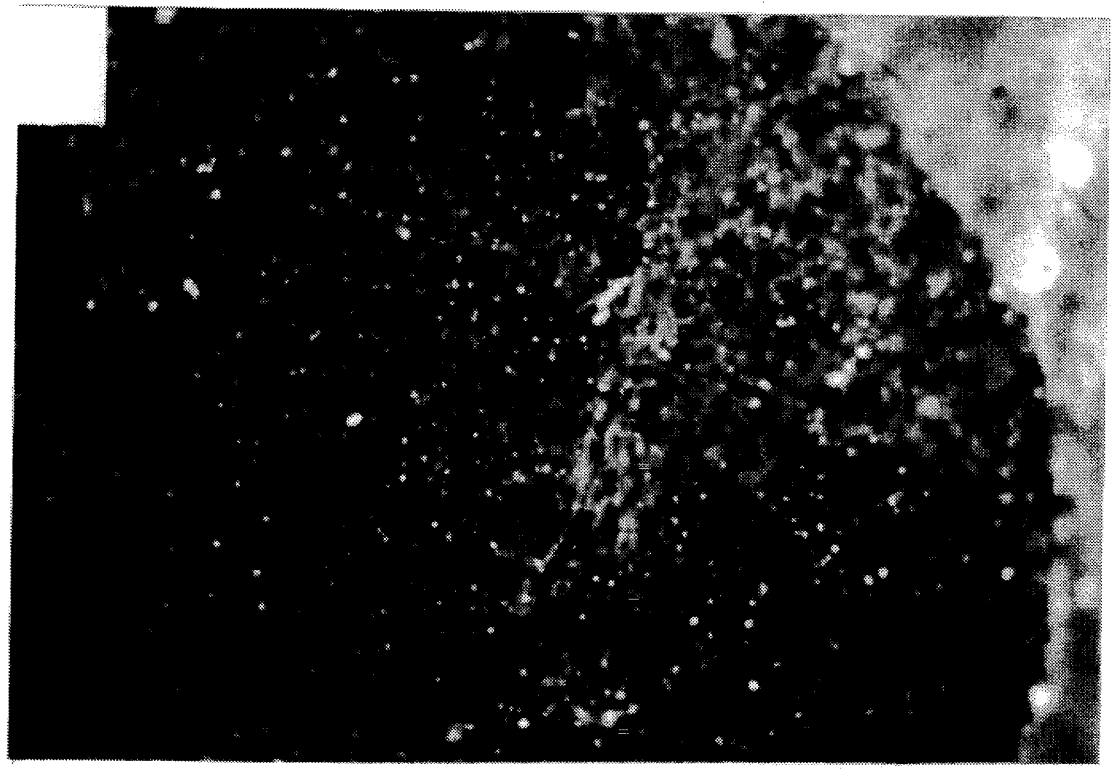

Slides were developed, counterstained with hematoxylin and eosin. Negative controls consisted of hybridization of serial sections with sense probes. As can be seen in FIG. 7, the antisense strand encoded by the isolated ligand cDNA clone clearly hybridizes to the HEV of peripheral lymphoid tissue, while the sense strand shows no significant hybridization. This result clearly demonstrates that the mRNA corresponding to the ligand cDNA is synthesized by HEV cells, consistent with previous immunohistochemical data demonstrating the localization of the L-selectin ligand to this region of the mesenteric and PLN.

The data described here are consistent with the hypothesis that an endothelial ligand for L-selectin is a unique mucin-type glycoprotein. Mucins, by definition, are serine/threonine rich proteins whose molecular weight is predominantly due to O-linked carbohydrate side chains (Cyster et al., The Embo J. 10:893 (1991), Fukuda, M., Glycobiology 1:347 (1991), Gendler et al., Am. Rev. Respir. Dis. 144:S42 (1991), Gum et al., The J. of Biol. Chem. 266:22733 (1991), Porchet et al., Am. Rev. Resp. Dis. 144:S15 (1991)). The high serine and threonine content found in the L-selectin ligand described here, coupled with the high degree of glycosylation of the protein (~70% by molecular weight), suggests that the bulk of the carbohydrates on the ligand are, in fact, O-linked and confirms previous experiments demonstrating N-glycanase resistance of the ~50 kD sulfated PLN ligand. The fact that the O-linked carbohydrates appear to be directly involved in the adhesive interactions mediated by the L-Selectin lectin domain suggests that the role of the protein backbone described here appears to be as a scaffold for carbohydrate presentation. This protein, therefore, represents a novel type of cell adhesion molecule that functions to present carbohydrates in a tissue-specific manner to the lectin domain of L-selectin. In this way, the regional expression of this "scaffold" may result in regional trafficking of lymphocyte populations.

The use of a mucin-like glycoprotein as a scaffold for carbohydrate presentation to a selectin makes sense when viewed in the context of what is currently known about mucin structure. Previous investigations into the structures of highly O-linked glycoproteins such as mucins have revealed that these molecules tend to be highly extended, somewhat rod-like molecules. For example, the leukocyte surface mucin leukosialin (sialophorin, CD43) (Cyster et al. 1991, Supra, Fukuda 1991, Supra), has been demonstrated to form a rigid, rod-like structure, and physicochemical analyses of other mucins have demonstrated similar rod-like conformations, particularly in the highly O-glycosylated regions (Harding, S. E., Advances in Carbohydrate Chemistry and Biochemistry 47:345 Academic Press, Inc. (1989), Jentoft, N., TIBS 15:291 (1990)). In addition, other non-mucin proteins, such as decay accelerating factor (DAF) and the low density lipoprotein (LDL) receptor contain highly O-linked domains near the cell surface that appear to form rod-like domains that may function to extend the receptors through the glycocalyx (Jentoft 1990, supra). This rod-like structure is exactly what would be 5 expected of a molecule whose role is to present carbohydrates to the lectin domain of a selectin. As shown in the model illustrated in FIG. 6, the L-selectin ligand may be thought of as a "bottle brush" that extends into the lumen of the HEV. This would allow for a large number of O-linked carbohydrate ligands (the bristles on the brush) to be appropriately presented to the lymphocyte surface-localized L-selectin lectin domain, thus mediating adhesion to the endothelium. The apparent clustering of these carbohydrates into 2 domains on the ligand suggests that they may be presented in a polyvalent manner to enhance the binding avidity of the lymphocyte-HEV adhesive interaction. The mucin-like nature of the L-selectin ligand could thus function to present polyvalent carbohydrate ligands to the L-selectin lectin domain via an extended, rod-like platform. If accurate, this would define a new mechanism of cell adhesion in the immune system.

The expression analysis described here suggests that the regulation of regional lymphocyte trafficking mediated by L-selectin may be due to the tissue specific expression of the ligand mRNA. We found that only those tissues that were previously described as mediating lymphocyte-HEV interactions via L-selectin expressed high levels of the mRNA for the ligand, although the extremely low level of mRNA in the Peyer's patch was somewhat unexpected Gallatin, Cell 44:673 (1986), Butcher, Am. J. Pathol, 136:3 (1990), Imai et al., J. Cell Biol. 113, 1213 (1991), Streeter et al., J. Cell Biol. 107, 1853 1988b, Woodruff et al., Annu. Rev. Immunol. 5, 201 (1987). These results are consistent with the possibility that regional trafficking is, at least in part, controlled by the transcriptional activation of the ligand mRNA described here, and suggest that exogenous factors may regulate L-selectin-mediated adhesion by controlling the transcription of the ligand gene. Of course, the protein backbone of the ligand is insufficient to mediate L-selectin adhesion, and it is possible that the genes controlling the glycosyl-transferases involved in making the carbohydrate ligand(s) found on this backbone may also be transcriptionally regulated. This latter possibility is now testable by investigating the activity of the ligand glycoprotein produced by expression of the cDNA described here in non-HEV cells. Another level of regulation may involve the mechanisms by which the ~50 kD ligand receives the appropriate L-selectin-specific carbohydrate side chains while other O-linked glycoproteins do not. The possibility that the L-selectin ligand described here can be ectopically expressed in chronic or acute inflammatory sites to mediate lymphocyte or neutrophil trafficking remains to be investigated (Watson et al., Nature 349:164 (1991)). It is possible that the extremely low level of ligand mRNA expression detected in the Peyer's patch is an indication of such regulatable ectopic expression.

Figure 8:
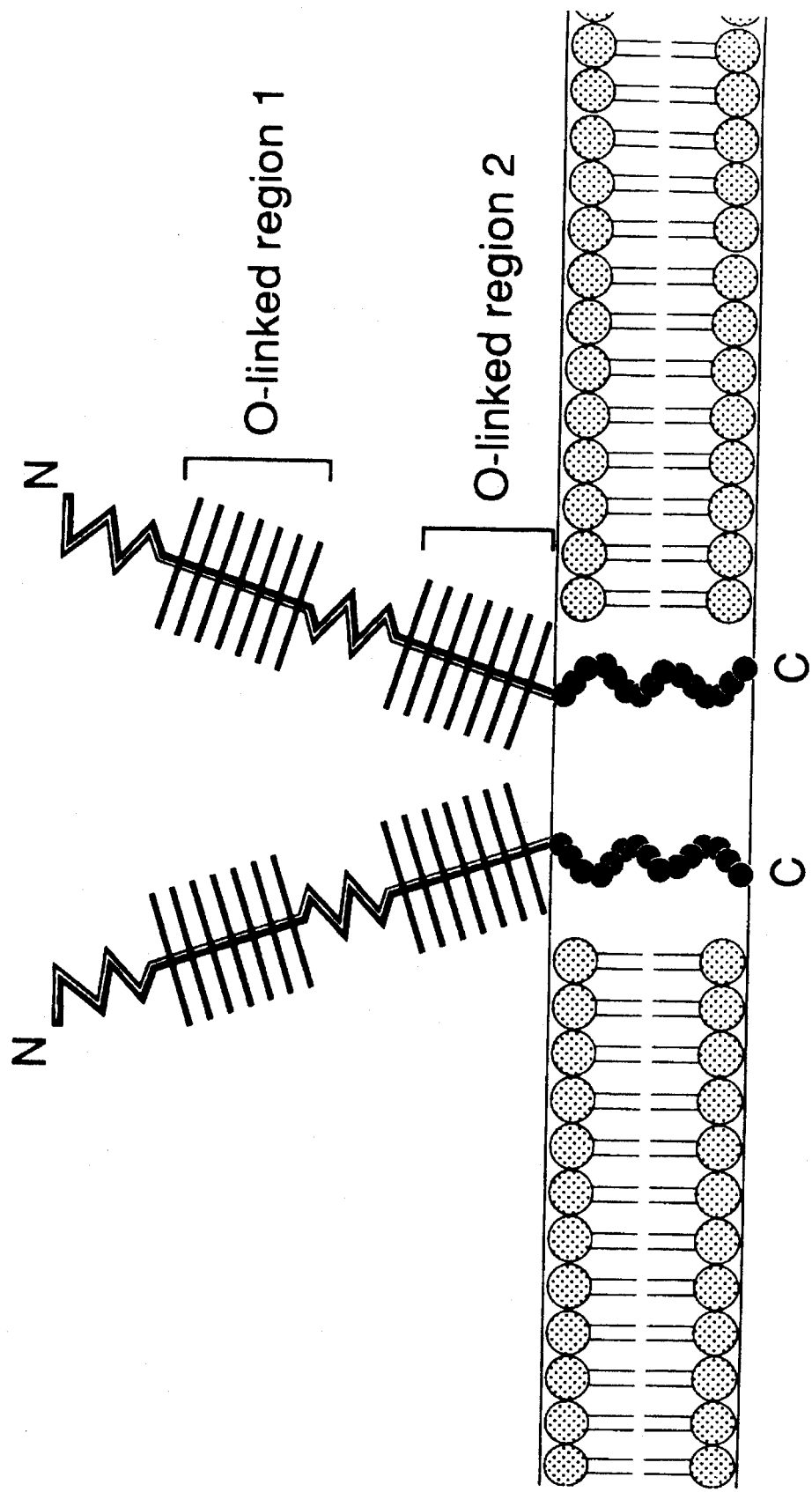
FIG. 8. A model of the structure of the ~50 kD Selectin ligand. Illustrated is one possible model for the structure of the ~50 kD L-selectin ligand on the luminal surface of the peripheral lymph node HEV. The extended brush-like regions correspond to O-linked regions I and II in a highly O-glycosylated state. The less-extended regions correspond to the N-terminal and central serine/threonine poor domains. In this model, membrane attachment is accomplished by oligomerization of the C-terminal amphipathic helical regions and insertion of these regions into the membranes so that the polar regions interact with each other to form an oligomer and the apolar faces of the helices interact with the lipid bilayer. As described in the text, a number of other models are also equally likely.

While it is clear that the ~50 kD ligand described here readily adheres to L-selectin via protein-carbohydrate interactions, the mechanism by which this ligand associates with the endothelial cell surface remains to be defined. The rapid shedding found here could be an artefact of organ culture, but other data demonstrating that an active shed form of the ligand can be purified from bovine (J. Gilbert-unpublished observations) or murine (S. Watson-unpublished observations) serum suggest that this ligand may be shed in vivo. A number of other cell surface adhesion molecules, including L- and P-selectins, Johnston et al., Cell 56, 1033 (1989)) and ICAM I (Rothlein et al., J. Immunol. 147:3788 (1991)), have been found to be shed, and it appears that in many cases the shedding is of physiological importance. The rapid shedding of the ligand reported here suggests a relatively loose association with the luminal surface of the HEV. One such association could be mediated by the amphipathic helix described above and illustrated in the model shown in FIG. 8. This helical region could span the membrane and simultaneously mediate membrane attachment and the formation of oligomeric forms of the ligand. That the ligand is capable of oligomerization has been found during gel filtration experiments (Y. Imai and S. Rosen-unpublished observations). A number of other proteins have been found to utilize amphipathic helices for membrane association and pore formation (Haffar et al., J. Cell Biol. 107:1677 [1988], Eisenberg et al., J. Mol. Biol. 179:125 [1984], Finer-Moore and Stroud, PROS, Natl. Acad. Sci. USA 81:155 [1984]), and it is therefore possible that this domain could function in a similar manner in the case of the L-selectin ligand. An alternative hypothesis is that the amphipathic helix could interact weakly with another protein that is more tightly associated with the endothelial cell surface. It is also possible that the ligand is incorporated into the glycocalyx in a currently ill-defined manner. A final possibility is that there are several HEV ligands that bind to the L-selectin lectin domain, some of which are tightly associated with the endothelial cell surface, such as the ~90 kD sulfated ligand described by Imai et al (1991), Supra or the PLN addressins described by Streeter et al., J. Cell Biol. 107, 1853 (1988b), and others, like the ~50 kD ligand described here, that are shed.

The relationship between the mucin-like endothelial ligand described here and the previously reported group of proteins defined by the monoclonal antibody MECA 79 (the pln "addressins" Streeter et al., Nature (Lond.) 331:41, J. Cell Biol. 107, 1853 [1988], Berg et al., Immunol. Rev. 108:5 [1991]) remains to be defined. Imai et al. (1991), Supra previously demonstrated that the ligand described here is recognized by the MECA 79 antibody (an antibody that binds an unknown carbohydrate determinant), but Streeter et al. (1988b), Supra and Berg et al. (1991), Supra have shown that a number of additional glycoproteins appear to also express this carbohydrate-like epitope. It is, therefore, possible that other endothelial glycoproteins exist that present carbohydrate to the L-selectin lectin domain. The development of monoclonal antibody reagents specific for the mucin-like ligand reported here will therefore be of great importance, since they will allow for an assessment of the relative contribution of this glycoprotein versus others as adhesive ligands for L-selectin-mediated trafficking.

The ~50 kD L-selectin ligand is the fourth type of molecule that is involved with cell adhesion in the immune system: 1) the leukocyte integrins, 2) their ligands, the immunoglobulin (Ig) superfamily members, 3) the selectins and 4) the ~50 kD L-selectin ligand. The integrins, Ig superfamily members, and selectins have all been found to comprise families containing a diversity of related molecules. Because of the characteristics of the ligand described here, we propose to replace the cumbersome nomenclature used throughout this application with the more descriptive term, GLYCAM 1 (GLYcosylation dependant Cell Adhesion Molecule).

All citations cited throughout the specification, and the references cited therein, are hereby expressly incorporated by reference.

Although the foregoing refers to particular preferred embodiments, it will be understood that the present invention is not so limited. It will occur to those ordinarily skilled in the art that various modifications may be made to the disclosed embodiments without diverting from the overall concept of the invention. All such modifications are intended to be within the scope of the present invention.

What is claimed is:

1. A purified polypeptide comprising an amino acid sequence encoded by a nucleic acid able to hybridize under low stringency conditions to the complement of a nucleotide sequence encoding the protein having the amino acid sequence shown in FIG. 4 (SEQ. ID. No.:2), capable of binding a native L-selectin.

2. The polypeptide of claim 1 which is Sgp50.

3. The polypeptide of claim 1 wherein the low stringency conditions are overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextrane sulfate, and 20 µg/ml denatured, sheared salmon sperm DNA.

4. The polypeptide of claim 1 which is an isolated native L-selectin ligand.

5. The polypeptide of claim 1 fused at its C-terminus to the N-terminus of an immunoglobulin constant domain sequence.

6. The polypeptide of claim 1 comprising amino acid positions 20 to 151, inclusive of the amino acid sequence shown in FIG. 4 (SEQ. ID. No.:2).

7. The polypeptide of claim 5 wherein said immunoglobulin is $IgG_1$, $IgG_2$ or $IgG_3$.

8. The polypeptide of claim 7 wherein the immunoglobulin constant domain sequence is the $C_H1$, hinge, $C_H2$ and $C_H3$ domains of an IgG1, IgG2, or IgG3 heavy chain.

9. The polypeptide of claim 7 wherein the immunoglobulin constant domain sequence is the hinge, $C_H2$ and $C_H3$ domains of an IgG1, IgG2, or IgG3 heavy chain.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 22 amino acids
( B ) TYPE: amino acid
( D ) TOPOLOGY: linear ( x i ) SEQUENCE DESCRIPTION: SEQ ID NO:1:

```
Leu Pro Gly Ser Xaa Asp Glu Leu Gln Met Lys Xaa Gln Xaa Met
 1               5                  10                  15

Asp Ala Ile Pro Ala Ala Gln
                20      22
```

( 2 ) INFORMATION FOR SEQ ID NO:2:

( i ) SEQUENCE CHARACTERISTICS:
( A ) LENGTH: 609 bases
( B ) TYPE: nucleic acid
( C ) STRANDEDNESS: single
( D ) TOPOLOGY: linear ( x i ) SEQUENCE DESCRIPTION: SEQ ID NO:2:

```
CTGACCTTGT  TCCAGTGCCA  CCATGAAATT  CTTCACTGTC  CTGCTATTTG   50

TCAGTCTTGC  TGCCACCTCT  CTTGCTCTCC  TGCCTGGGTC  CAAAGATGAA  100

CTTCAAATGA  AGACTCAGCC  CACAGATGCC  ATTCCAGCTG  CCCAGTCCAC  150

TCCCACCAGC  TACACCAGTG  AGGAGAGTAC  TTCAGTAAG   GACCTTTCCA  200

AGGAGCCTTC  CATCTTCAGA  GAAGAGCTGA  TTTCCAAAGA  TAATGTGGTG  250
```

-continued

```
         ATAGAATCTA  CCAAGCCAGA  GAATCAAGAG  GCCCAGGATG  GGCTCAGGAG   300

CGGGTCATCT  CAGCTGGAAG  AGACCACAAG  ACCCACCACC  TCAGCTGCAA   350

CCACCTCAGA  GGAAAATCTG  ACCAAGTCAA  GCCAGACAGT  GGAGGAAGAA   400

CTGGGTAAAA  TAATTGAAGG  ATTTGTAACT  GGTGCAGAAG  ACATAATCTC   450

TGGTGCCAGT  CGTATCACGA  AGTCATGAAG  ACAAAAACAC  CTAACCACTA   500

AGTCCCATGC  TAGGTGGTGC  CTTCATCAGC  CACATTCTGC  TCATCTGACC   550

ACCACCTCTC  AGTCTGCCCT  TTGATGTCTT  ACATTAAAGT  ATTGCAACCT   600

AAAAAAAA    609
```

( 2 ) INFORMATION FOR SEQ ID NO:3:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:3:

```
Gln  Met  Lys  Thr  Gln  Xaa  Met  Asp  Ala
 1                  5                   9
```

( 2 ) INFORMATION FOR SEQ ID NO:4:

( i ) SEQUENCE CHARACTERISTICS:
        ( A ) LENGTH: 12 amino acids
        ( B ) TYPE: amino acid
        ( D ) TOPOLOGY: linear ( x i ) SEQUENCE DESCRIPTION: SEQ ID NO:4:

```
Leu  Pro  Ser  Lys  Asp  Glu  Leu  Gln  Met  Lys  Thr  Cys
 1                  5                        10        12
```

( 2 ) INFORMATION FOR SEQ ID NO:5:

( i ) SEQUENCE CHARACTERISTICS:
        ( A ) LENGTH: 15 amino acids
        ( B ) TYPE: amino acid
        ( D ) TOPOLOGY: linear ( x i ) SEQUENCE DESCRIPTION: SEQ ID NO:5:

```
Cys  Lys  Glu  Pro  Ser  Ile  Phe  Arg  Glu  Glu  Leu  Ile  Ser  Lys  Asp
 1                  5                        10                       15
```

( 2 ) INFORMATION FOR SEQ ID NO:6:

( i ) SEQUENCE CHARACTERISTICS:
        ( A ) LENGTH: 12 amino acids
        ( B ) TYPE: amino acid
        ( D ) TOPOLOGY: linear ( x i ) SEQUENCE DESCRIPTION: SEQ ID NO:6:

```
Cys  Ile  Ile  Ser  Gly  Ala  Ser  Arg  Ile  Thr  Lys  Ser
 1                  5                        10        12
```